(12) United States Patent
Boppart et al.

(10) Patent No.: US 7,623,908 B2
(45) Date of Patent: Nov. 24, 2009

(54) NONLINEAR INTERFEROMETRIC VIBRATIONAL IMAGING

(75) Inventors: Stephen A. Boppart, Champaign, IL (US); Daniel L. Marks, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 911 days.

(21) Appl. No.: 10/717,437

(22) Filed: Nov. 19, 2003

(65) Prior Publication Data

US 2005/0168735 A1   Aug. 4, 2005

Related U.S. Application Data

(60) Provisional application No. 60/442,300, filed on Jan. 24, 2003.

(51) Int. Cl.
*A61B 6/00* (2006.01)
(52) U.S. Cl. ...................... 600/477; 356/460
(58) Field of Classification Search ........... 600/407, 600/410, 437, 476, 477; 356/450, 451, 452, 356/453, 456, 460
See application file for complete search history.

(56) References Cited

U.S. PATENT DOCUMENTS

| | | | |
|---|---|---|---|
| 4,522,811 A | 6/1985 | Eppstein et al. | |
| 5,095,487 A | 3/1992 | Meyerhofer et al. | |
| 5,247,343 A | 9/1993 | Burch | |
| 5,303,710 A | 4/1994 | Bashkansky et al. | |
| 5,362,478 A | 11/1994 | Desai et al. | |
| 5,439,686 A | 8/1995 | Desai et al. | |
| 5,451,785 A * | 9/1995 | Faris | 250/330 |
| 5,459,570 A | 10/1995 | Swanson et al. | |
| 5,498,421 A | 3/1996 | Grinstaff et al. | |

(Continued)

FOREIGN PATENT DOCUMENTS

WO   WO 90/01697   2/1990

(Continued)

OTHER PUBLICATIONS

Sadtler et al., "Spherical ensembles of gold nanoparticles on silica: electrostatic and size effects", Chem. Commun., 1604-05, 2002.

(Continued)

*Primary Examiner*—Brian Casler
*Assistant Examiner*—Joel M Lamprecht
(74) *Attorney, Agent, or Firm*—Sunstein Kann Murphy & Timbers LLP

(57) ABSTRACT

A method of examining a sample, which includes: exposing a reference to a first set of electromagnetic radiation, to form a second set of electromagnetic radiation scattered from the reference; exposing a sample to a third set of electromagnetic radiation to form a fourth set of electromagnetic radiation scattered from the sample; and interfering the second set of electromagnetic radiation and the fourth set of electromagnetic radiation. The first set and the third set of electromagnetic radiation are generated from a source; at least a portion of the second set of electromagnetic radiation is of a frequency different from that of the first set of electromagnetic radiation; and at least a portion of the fourth set of electromagnetic radiation is of a frequency different from that of the third set of electromagnetic radiation.

35 Claims, 15 Drawing Sheets

U.S. PATENT DOCUMENTS

| | | | |
|---|---|---|---|
| 5,505,932 A | 4/1996 | Grinstaff et al. | |
| 5,508,021 A | 4/1996 | Grinstaff et al. | |
| 5,512,268 A | 4/1996 | Grinstaff et al. | |
| 5,560,933 A | 10/1996 | Soon-Shiong et al. | |
| 5,635,207 A | 6/1997 | Grinstaff et al. | |
| 5,639,473 A | 6/1997 | Grinstaff et al. | |
| 5,648,506 A | 7/1997 | Desai et al. | |
| 5,650,156 A | 7/1997 | Grinstaff et al. | |
| 5,665,382 A | 9/1997 | Grinstaff et al. | |
| 5,665,383 A | 9/1997 | Grinstaff et al. | |
| 5,914,806 A | 6/1999 | Gordon II et al. | |
| 5,930,026 A | 7/1999 | Jacobson et al. | |
| 5,972,493 A | 10/1999 | Iwasaki et al. | |
| 5,994,690 A * | 11/1999 | Kulkarni et al. | 250/216 |
| 6,002,480 A * | 12/1999 | Izatt et al. | 356/479 |
| 6,037,579 A * | 3/2000 | Chan et al. | 250/216 |
| 6,068,600 A | 5/2000 | Johnson et al. | |
| 6,091,496 A * | 7/2000 | Hill | 356/491 |
| 6,108,081 A | 8/2000 | Holtom et al. | |
| 6,134,003 A * | 10/2000 | Tearney et al. | 356/479 |
| 6,156,292 A | 12/2000 | Quay | |
| 6,159,445 A | 12/2000 | Klaveness et al. | |
| 6,208,886 B1 | 3/2001 | Alfano et al. | |
| 6,219,137 B1 | 4/2001 | Vo-Dinh | |
| 6,231,834 B1 | 5/2001 | Unger et al. | |
| 6,246,892 B1 | 6/2001 | Chance | |
| 6,246,901 B1 | 6/2001 | Benaron | |
| 6,249,271 B1 | 6/2001 | Albert et al. | |
| 6,262,706 B1 | 7/2001 | Albert et al. | |
| 6,262,833 B1 | 7/2001 | Loxley et al. | |
| 6,264,917 B1 | 7/2001 | Klaveness et al. | |
| 6,264,918 B1 | 7/2001 | Johnson et al. | |
| 6,280,704 B1 | 8/2001 | Schutt et al. | |
| 6,300,932 B1 | 10/2001 | Albert | |
| 6,307,633 B1 | 10/2001 | Mandella et al. | |
| 6,307,634 B2 | 10/2001 | Hitzenberger et al. | |
| 6,312,304 B1 | 11/2001 | Duthaler et al. | |
| 6,315,981 B1 | 11/2001 | Unger | |
| 6,344,272 B1 | 2/2002 | Oldenburg et al. | |
| 6,363,163 B1 | 3/2002 | Xu et al. | |
| 6,428,811 B1 | 8/2002 | West et al. | |
| 6,485,413 B1 | 11/2002 | Boppart et al. | |
| 6,514,767 B1 | 2/2003 | Natan | |
| 6,529,277 B1 | 3/2003 | Weitekamp | |
| 6,530,944 B2 | 3/2003 | West et al. | |
| 6,538,805 B1 | 3/2003 | Norwood et al. | |
| 6,539,156 B1 | 3/2003 | Dickson et al. | |
| 6,564,087 B1 | 5/2003 | Pitris et al. | |
| 6,574,401 B2 | 6/2003 | Neuberger et al. | |
| 6,584,335 B1 | 6/2003 | Haar et al. | |
| 6,618,423 B1 | 9/2003 | Dekorsy et al. | |
| 6,795,777 B1 | 9/2004 | Scully et al. | |
| 6,825,928 B2 | 11/2004 | Liu et al. | |
| 6,839,586 B2 | 1/2005 | Webb | |
| 2002/0028993 A1 | 3/2002 | Hainfeld | |
| 2002/0054912 A1 | 5/2002 | Kim et al. | |
| 2002/0087071 A1 | 7/2002 | Schmitz et al. | |
| 2002/0168161 A1 | 11/2002 | Price et al. | |
| 2003/0045798 A1 | 3/2003 | Hular et al. | |
| 2003/0068496 A1 | 4/2003 | Wei et al. | |
| 2003/0082104 A1 | 5/2003 | Mertelmeier | |
| 2004/0023415 A1 | 2/2004 | Sokolov et al. | |
| 2004/0024307 A1 | 2/2004 | Golman et al. | |
| 2004/0058458 A1 | 3/2004 | Anker et al. | |
| 2004/0186359 A1 | 9/2004 | Beaudoin et al. | |
| 2004/0249268 A1 | 12/2004 | Da Silva | |
| 2005/0004453 A1 | 1/2005 | Tearney et al. | |
| 2005/0078363 A1 | 4/2005 | Gugel | |
| 2005/0149002 A1 | 7/2005 | Wang et al. | |
| 2005/0168735 A1 | 8/2005 | Boppart et al. | |
| 2005/0171433 A1 | 8/2005 | Boppart et al. | |
| 2006/0066848 A1 | 3/2006 | Frankel | |
| 2006/0192969 A1 | 8/2006 | Marks et al. | |
| 2006/0285635 A1 | 12/2006 | Boppart et al. | |
| 2006/0292839 A1 | 12/2006 | Yi et al. | |
| 2007/0203404 A1 | 8/2007 | Zysk et al. | |

FOREIGN PATENT DOCUMENTS

| | | |
|---|---|---|
| WO | WO 00/42906 | 7/2000 |
| WO | WO 00/42912 | 7/2000 |
| WO | WO 02/088705 | 11/2002 |
| WO | WO 2007/027194 | 3/2007 |
| WO | WO 2007/090147 | 9/2007 |

OTHER PUBLICATIONS

Tearney et al., "High-Speed Phase- and Group-Delay Scanning with a Grating-Based Phase Control Delay Line", Optics Letters, vol. 22, No. 23 :1811-1813, 1997.

Templeton et al., "Monolayer-protected cluster molecules", Acc. Chem. Res., 33:27-36, 2000.

Timmerman et al., "Resorcinarenes" Tetrahedron, 52:2663-704, 1996.

Tkachenko et al., "Multifunctional Gold Nanoparticle-Peptide Complexes for Nuclear Targeting", J. Am. Chem. Soc., 125:4700-4701, 2003.

Wang et al., "Use of a Laser Beam with an Oblique Angle of Incidence to Measure the Reduced Scattering Coefficient of a Turbid Medium", Applied Optics, 34:2362-2366, 1995.

Webb et al., "Sonochemically produced fluorocarbon microspheres: a new class of magnetic resonance imaging agent", J. Magnetic Resonance Imaging, 6:675-683, 1996.

Wei et al., "Resorcinarene-encapsulated nanoparticles: building blocks for self-assembled nanostructures", J. Inclusion Phenomenal Macrocyclic Chemistry, 41, 83-86, 2001.

Wei et al., "Synthesis and Characterization of Resorcinarene-Encapsulated Nanoparticles", Mater. Res. Soc., Symp. Proc. Ser., 581:59-63, 1999.

Wei et al., "Tunable Surface-Enhanced Raman Scattering from Large Gold Nanoparticle Arrays", ChemPhysChem., 2:743-45, 2001.

Wong et al., "Sonochemically produced hemoglobin microbubbles", Mat. Res. Soc. Symp. Proc., 372:89-94, 1995.

Zaheer et al., "In vivo near-infrared fluorescence imaging of osteoblastic activity", Nature Biotechnology, 19:1148-54, 2001.

Marks et al., "Interferometric differentiation between resonant Coherent Anti-Stokes Raman Scattering and nonresonant four-wave-mixing processes", arXiv:physics/0403007, pp. 1-8, 2004.

Vinegoni et al., "Nonlinear optical contrast enhancement for optical coherence tomography", Optics Express, vol. 12, No. 2, p. 331-341, 2004.

Kee et al., "Simple approach to one-laser, broadband coherent anti-Stokes Raman scattering microscopy", Optics Letters, vol. 29, No. 23, p. 2701-2703, 2004.

Kano et al., "Vibrationally resonant imaging of a single living cell by supercontinuum-based multiplex coherent anti-Stokes Raman scattering microspectroscopy", Optics Express, vol. 13, Issue 4, pp. 1322-1327, 2005.

Gao et al., "Formulation, Characterization, and Sensing Applications of Transparent Poly(vinyl alcohol)-Polyelectrolyte Blends", Chem. Mater., 10, pp. 2481-2489, 1998.

Marks et al., Molecular Species Sensitive Optical Coherence Tomography Using Coherent Anti-Stokes Raman Scattering Spectroscopy, Coherence Domain Optical Methods and Optical Coherence Tomography In Biomedicine VII, Proceedings of SPIE, vol. 4956, pp. 9-13, 2003.

Bredfeldt et al., "Non-linear interferometric vibrational imaging", Conference on Lasers and Electro-optics, CLEO '03, pp. 309-311, 2003.

Vinegoni et al., "Nonlinear optical contrast enhancement for optical coherence tomography", http://www.arxiv.org/abs/physics/0312114, 13 pages (2003).

Zumbusch et al., "Three-dimensional vibrational imaging by coherent anti-Stokes Raman scattering", Phys. Rev. Lett., 82(20), pp. 4142-4145, 1999.

Cheng et al., "An epi-detected coherent anti-Stokes Raman scattering (E-CARS) microscope with high spectral resolution and high sensitivity", J. Phys. Chem, 105(7), pp. 1277-1280, 2001.

Hashimoto et al., "Molecular vibration imaging in the fingerprint region by use of coherent anti-Stokes Raman scattering microscopy with a collinear configuration", Opt. Lett., 25(24), pp. 1768-1770, 2000.

Volkmer et al., "Vibrational imaging with high sensitivity via epidected coherent anti-Stokes Raman scattering microscopy", Phys. Rev. Lett., 87(2):023901-1-4, 2001.

Schmitt et al. "Optical-coherence tomography of a dense tissue: statistics of attenuation and backscattering", Phys. Med. Biol., vol. 39, pp. 1705-1720, (1994).

Tearney et al., "In vivo endoscopic optical biopsy with optical coherence tomography", Science, vol. 276, pp. 2037-2039, (1997).

Fantini et al., "Assessment of the size, position, and optical properties of breast tumors in vivo by noninvasive optical methods", Applied Optics, vol. 37, pp. 1982-1989, 1998.

Faber et al., "Quantitative measurement of attenuation coefficients of weakly scattering media using optical coherence tomography", Optics Express, 12(19), pp. 4353-4365, 2004.

Fujimoto et al., "Optical Coherence Tomography: An Emerging Technology for Biomedical Imaging and Optical Biopsy", Neoplasia, 2(1-2), pp. 9-25, 2000.

Zysk et al., "Computational methods for analysis of human breast tumor tissue in optical coherence tomography images", Journal of Biomedical Optics, 11(5), 054015-1-054015-7, 2006.

Levitz et al., "Determination of optical scattering properties of highly-scattering media in optical coherence tomography images", Optics Express, 12(2), pp. 249-259, 2004.

Morgner et al., "Spectroscopic optical coherence tomography", Optics Letters, 25(2), pp., 111-113, 2000.

Gossage et al., "Texture analysis of optical coherence tomography images: feasibility for tissue classification", Journal of Biomedical Optics, 8(3), pp. 570-575, 2003.

Zvyagin et al., "Refractive index tomography of turbid media by bifocal optical coherence refractometry", Optics Express, 11(25), pp. 3503-3517, 2003.

Gottschalk, "Ein Meβverfahren zur Bestimmung der optischen Parameter biologisher Gewebe in vitro", Dissertation 93 HA 8984, Universität Fridericiana Karlsruhe, 1993.

Bolin, F.P. et al., "Refractive index of some mammalian tissues using a fiber optic cladding method", Applied Optics, 28, pp. 2297-2303, 1989.

Tearney et al., "Determination of the refractive index of highly scattering human tissue by optical coherence tomography", Optics Letters, 20(21), pp. 2258-2260, 1995.

Zysk et al., "Needle-based refractive index measurement using low-coherence interferometry", Optics Letters, 32, pp. 385-387, 2007.

Zysk et al., "Refractive index of carcinogen-induced rat mammary tumours", Phys. Med. Biol., 51, pp. 2165-2177, 2006.

Li et al., "Measurement method of the refractive index of biotissue by total internal reflection", Applied Optics, 35, pp. 1793-1795, 1996.

Knuttel et al., "Spatially confined and temporally resolved refractive index and scattering evaluation in human skin performed with optical coherence tomography", Journal of Biomedical Optics, 5, pp. 83-92, 2000.

Boppart et al., "Optical coherence tomography: feasibility for basic research and image-guided surgery of breast cancer", Breast Cancer Research and Treatment, vol. 84, pp. 85-97, 2004.

Liberman et al., "Palpable breast masses: Is there a role for percutaneous image-guided core biopsy?", American Journal of Roentgenology, vol. 175, pp. 779-787, 2000.

Bolivar et al., "Stereotaxic core needle aspiration biopsy with multiple passes in nonpalpable breast lesions", Acta Radiologica, vol. 39, pp. 389-394, 1998.

Acheson et al., "Histologic correlation of image-guided core biopsy with excisional biopsy of nonpalpable breast lesions", Archives of Surgery, vol. 132, pp. 815-821, 1997.

Pijnappel et al., "The diagnostic accuracy of core biopsy in palpable and non-palpable breast lesions", European Journal of Radiology, vol. 24, pp. 120-123, 1997.

Durduran et al., "Bulk optical properties of healthy female breast tissue", Physics in Medicine and Biology, vol. 47, pp. 2847-2861, 2002.

International Search Report dated Feb. 15, 2007 for International Application No. PCT/US2006/006618, 5 pages.

Marks et al., "Interferometric differentiation between resonant coherent anti-Stokes Raman scattering and nonresonant four-wave-mixing processes", Applied Physics Letters, vol. 85, No. 23, pp. 5787-5789. 2004.

Marks et al., "Nonlinear Interferometric Vibrational Imaging", Physical Review Letters, vol. 92, No. 12, pp. 123905-1-123905-4, 2004.

Boppart et al., "Contrast Enhancement Methods for Optical Coherence Tomography", Biophotonics/Optical Interconnects and VLSI Photonics/WBM Microactivities, 2004 Digest of the Leos Summer Topical Meetings, San Diego, CA, pp. 14-15, 2004.

Marks et al., "Pulse Shaping Strategies for Nonlinear Interferometric Vibrational Imaging Optimized for Biomolecular Imaging", Proceedings of the 26th Annual International Conference of the IEEE EMBS, San Francisco, CA, pp. 5300-5303, 2004.

Bredfeldt et al., "Nonlinear interferometric vibrational imaging of molecular species", Proc. Of SPIE, vol. 5321, pp. 149-156, 2004.

Easy Core Biopsy System, Product Brochure, Boston Scientific, 5 pages, 2004.

Yodh et al., "Spectroscopy and Imaging with Diffusing Light," Physics Today, pp. 34-40, 1995.

Roggan et al., in "Laser Induced Interstitial Thermotherapy", Muller, Ed., pp. 39-40,43, 1995.

Ohmi et al., "In Vitro Simultaneous Measurement of Refractive Index and Thickness of Biological Tissue by the Low Coherence Interferometry", IEEE Transactions on Biomedical Engineering, vol. 47, No. 9, pp. 1266-1270, 2000.

Luo et al., "Optical Biopsy of Lymph Node Morphology using Optical Coherence Tomography", Technology in Cancer Research & Treatment, vol. 4, No. 5, pp. 539-547, 2005.

Dehghani et al., "The effects of internal refractive index variation in near-infrared optical tomography: a finite element modelling approach", Physics in Medicine and Biology, 48, pp. 2713-2727, 2003.

Schmitt et al., "Turbulent nature of refractive-index variations in biological tissue", Optics Letters, vol. 21, No. 16, pp. 1310-1312, 1996.

Zysk et al., "Projected index computed tomography", Optics Letters, vol. 28, No. 9, pp. 701-703, 2003.

Easy Core Biopsy System, Product Brochure, Boston Scientific, 4 pages, 2004.

Evans et al., "Coherent anti-Stokes Raman scattering spectral interferometry: determination of the real and imaginary components of nonlinear susceptibility chi(3) for vibrational microscopy", Optics Letters, vol. 29, No. 24, pp. 2923-2925, 2004.

Yoon et al., "Dependence of line shapes in femtosecond broadband stimulated Raman spectroscopy on pump-probe timed delay", J Chem Phys., 122(2), p. 024505, 2005, 20 pages.

Kolomoitsev et al., "New problems of femtosecond time-domain CARS of large molecules", SPIE vol. 1402, pp. 31-43, 1990.

Mehendale et al, "Towards an anthrax detector using the femtosecond adaptive spectroscopic technique for coherent anti-Stokes Raman Spectroscopy: coherent anti-Stokes Raman spectroscopy signal from dipicolinic acid in bacterial spores", Journal of Modern Optics, vol. 51, pp. 2645-2653, 2004.

Boppart et al., "Intraoperative Assessment of Microsurgery with Three-Dimensional Optical Coherence Tomography," Radiology, 1998, pp. 81-86, vol. 208.

Boppart et al., "Optical Coherence Tomography for Neurosurgical Imaging of Human Intracortical Melanoma," Neurosurgery, 1998, pp. 834-841, vol. 43.

Boppart et al., "Forward-Imaging Instruments for Optical Coherence Tomography," Opt. Lett., 1997, pp. 1618-1620, vol. 22.

Boppart et al., "Investigation of Developing Embryonic Morphology Using Optical Coherence Tomography," Dev. Biol., 1996, pp. 54-63, vol. 177.

Boppart et al., "Imaging Developing Neural Morphology Using Optical Coherence Tomography," J. Neurosci. Meth., 1996, pp. 65-72, vol. 2112.
Boppart et al., "Noninvasive Assessment of the Developing *Xenopus* Cardiovascular System Using Optical Coherence Tomography," Proc. Natl. Acad. Sci. USA, 1997, pp. 4256-4261, vol. 94.
Boppart et al., "In vivo Cellular Optical Coherence Tomography Imaging," Nature Med., 1998, pp. 861-864, vol. 4.
Bouma et al., "High Resolution Optical Coherence Tomographic Imaging Using a Modelocked Ti:$Al_2O_3$ Laser,", Opt. Lett., 1995, pp. 1486-1488, vol. 20.
Bouma et al., "High-Resolution Imaging of the Human Esophagus and Stomach in vivo Using Optical Coherence Tomography," Gastrointest. Endosc., 2000, pp. 467-474, vol. 51.
Brezinski et al., "Optical Coherence Tomography for Optical Biopsy: Properties and Demonstration of Vascular Pathology," Circulation, 1996, pp. 1206-1213, vol. 93.
Chen et al., "Noninvasive Imaging of in vivo Blood Flow Velocity Using Optical Doppler Tomography," Opt. Lett., 1997, pp. 1119-1121, vol. 22.
De Boer et al., "Two-Dimensional Birefringence Imaging in Biological Tissue by Polarization Sensitive Optical Coherence Tomography," Opt. Lett., 1997, pp. 934-936, vol. 22.
Drexler et al., "In vivo Ultrahigh Resolution Optical Coherence Tomography," Opt. Lett., 1999, pp. 1221-1223, vol. 24.
Fujimoto et al., "Biomedical Imaging and Optical Biopsy Using Optical Coherence Tomography," Nature Medicine, 1995, pp. 970-972, vol. 1.
Hee et al., "Optical Coherence Tomography of the Human Retina," Arch. Ophthalmol., 1995, pp. 325-332, vol. 113.
Huang et al., "Optical Coherence Tomography," Science, 1991, pp. 1178-1181, vol. 254.
Pitris et al., "High Resolution Imaging of Gynecological Neoplasms Using Optical Coherence Tomography," Obstet. Gynecol., 1999, pp. 135-139, vol. 93.
Pitris et al., "Feasibility of Optical Coherence Tomography for High Resolution Imaging of Human Gastrointestinal Tract Malignancies," J. Gastroenterol., 1999, pp. 87-92, vol. 35.
Profio et al., "Transport of Light in Tissue in Photodynamic Therapy of Cancer," Protochem. Photobiol., 1987, pp. 591-599, vol. 46.
Puliafito et al., "Imaging of Macular Disease with Optical Coherence Tomography (OCT)," Ophthalmology, 1995, pp. 217-229, vol. 102.
Schmitt et al., "Optical Coherence Tomography of a Dense Tissue: Statistics of Attenuation and Backscattering," Phys. Med. Biol., 1994, pp. 1705-1720, vol. 39.
Schmitt et al., "Measurements of Optical Properties of Biological Tissues by Low-Coherence Reflectometry," Appl. Opt., 1993, pp. 6032-6042, vol. 32.
Sergeev et al., "In vivo Endoscopic OCT Imaging of Precancer and Cancer States of Human Mucosa," Opt. Express, 1997, pp. 432-440, vol. 1.
Sivak et al., "High-Resolution Endoscopic Imaging of the Gastrointestinal Tract Using Optical Coherence Tomography," Gastrointest. Endosc., 2000, pp. 474-479, vol. 51.
Tearney et al., "Scanning Single-Mode Fiber Optic Catheter-Endoscope for Optical Coherence Tomography," Opt. Lett., 1996, pp. 543-545, vol. 21.
Tearney et al., "In vivo Endoscopic Optical Biopsy with Optical Coherence Tomography," Science, 1997, pp. 2037-2039, vol. 276.
Tearney et al., "Optical Biopsy in Human Urologic Tissue Using Optical Coherence Tomography," J. Urol., 1997, pp. 1915-1919, vol. 157.
Tearney et al., "Rapid Acquisition of in vivo Biological Images Using Optical Coherence Tomography," Opt. Lett., 1996, pp. 1408-1410, vol. 12.
Yazdanfar et al., "High Resolution Imaging of in vivo Cardiac Dynamics Using Color Doppler Optical Coherence Tomography," Opt. Express, 1997, pp. 424-431, vol. 1.
Tearney et al., "Optical Biopsy in Human Gastrointestinal Tissue Using Optical Coherence Tomography," Am. J. Gastroenter., 1997, pp. 1800-1804, vol. 92.
Schmitt et al., "Subsurface Imaging of Living Skin with Optical Coherence Microscopy," Dermatology, 1995, pp. 93-98, vol. 191.
Li et al., "Optical Coherence Tomography: Advanced Technology for the Endoscopic Imaging of Barrett's Esophagus," Endoscopy, 2000, pp. 921-930, vol. 32.
Boppart, "Surgical Diagnostics, Guidance, and Intervention Using Optical Coherence Tomography," Thesis, Harvard-MIT Division of Health Sciences and Technology, Department of Electrical Engineering and Computer Science, Massachusetts Institute of Technology, Cambridge, MA, 1998 (226 pages).
Ai et al., "Electrostatic layer-by-layer nanoassembly on biological microtemplates: platelets", Biomacromolecules, 3:560-564, 2002.
Amsden et al., "An examination of factors affecting the size, distribution, and release characteristics of polymer microbeads made using electrostatics", J. Control. Release, 43:183-196, 1997.
Amsden, "The production of uniformly sized polymer microspheres", Pharm. Res., 16:1140-1143, 1999.
Balasubramanian et al., "Extraction and dispersion of large gold nanoparticles in nonpolar solvents", J. Dispers. Sci. Tech. 22:485-89, 2001.
Balasubramanian et al., "Dispersion and stability studies of resorcinarene-encapsulated gold nanoparticles", Langmuir, 18:3676-81, 2002.
Barton et al., "Use of microbubbles as an optical coherence tomography contrast agent", Acad. Radiol, 9, (Suppl 1):552-555, 2002.
Blackwell et al., "New approaches to olefin cross-metathesis", J. Am. Chem. Soc., 122:58-71, 2000.
Boppart et al., "High-Resolution Optical Coherence Tomography-Guided Laser Ablation of Surgical Tissue", J. Surgical Research, 82:275-84, 1999.
Boppart, "Endoscopic Optical Coherence Tomography Imaging of Barrett's Esophagus", M.D. Thesis, Harvard University, 2000.
Boyer et al., "Photothermal Imaging of Nanometer-Sized Metal Particles Among Scatterers", Science, 297:1160-63, 2002.
Bugaj et al., "Novel fluorescent contrast agents for optical imaging of in vivo tumors based on a receptor-targeted dye-peptide conjugate platform", J. Biomedical Optics, 6:122-33, 2001.
Burns et al., "Tumor-localizing and photosensitizing properties of hematoporphyrin derivative in hamster buccal pouch carcinoma", Oral Surg. Oral Med. Oral Pathol., 61:368-372, 1986.
Cain et al., "Thresholds for Visible Lesions in the Primate Eye Produced by Ultrashort Near-Infrared Laser Pulses", Investigative Ophthalmology & Visual Science, 40:2343-49, 1999.
Cain et al., "Visible Retinal Lesions from Ultrashort Laser Pulses in the Primate Eye", Investigative Ophthalmology & Visual Science, 36:879-888, 1995.
Caruso et al., "Nanoengineering of inorganic and hybrid hollow spheres by colloidal templating", Science, 282:1111-1114, 1998.
Cepak et al., "Preparation and Stability of Template-Synthesized Metal Nanorod Sols in Organic Solvents", J. Phys. Chem. B, 102:9985-90, 1998.
Christiansen et al., "Physical and biochemical characterization of Albunex™, a new ultrasound contrast agent consisting of air-filled albumin microparticles suspended in a solution of human albumin", Biotechnol. Appl. Biochem., 19:307-20, 1994.
Clark et al., "Second harmonic generation properties of fluorescent polymer-encapsulated gold nanoparticles", J. Am. Chem. Soc., 122:10234-35, 2000.
Decher "Fuzzy Nanoassemblies: Toward Layered Polymeric Multicomposites", Science, 277:1232-1237, 1997.
Desai et al., "Controlled and targeted drug delivery with biocompatible protein shell microspheres", 20th Annual Meeting of Society of Biomaterials, Apr. 4-9, 1994, Boston, MA: Proc. Soc. Biomaterial, 20:112, 1994.
Dick et al., "Computed tomography of experimental liver abscesses using a new liposomal contrast agent", Investigative Radiology, 31:194-203, 1996.
Dowlatshahi et al., "Histologic Evaluation of Rat Mammary Tumor Necrosis by Interstitial Nd:YAG Laser Hyperthermia", Lasers in Surgery and Medicine, 12:159-164, 1992.
El-Sayed "Some interesting properties of metals confined in time and nanometer space of different shapes", Accounts of Chemical Research, 34:257-64, 2001.

Freeman et al., "Self-Assembled Metal Colloid Monolayers: An Approach to SERS Substrates", Science, 267:1629-1632, 1995.

Fu et al., "Visual evidence of acidic environment within degrading poly(lactic-co-glycolic acid) (PLGA) microspheres", Pharmaceutical Research, 17:100-106, 2000.

Gazelle et al., "Nanoparticulate computed tomography contrast agents for blood pool and liver-spleen imaging", Acad. Radiol., 1:373-376, 1994.

Geny et al., "Safety of a new transpulmonary echocontrast agent (Albunex®) in repeated echocardiographic studies in patients", Clin. Cardiol., 20:111-115, 1997.

Gimenez-Conti et al., "The hamster cheek pouch carcinogenesis model", J. Cellular Biochemistry Supplement, 17F:83-90, 1993.

Gram, "Drug absorption and distribution", in Modern Pharmacology with Clinical Applications 5$^{th}$ Ed., Craig et al., eds., Little, Brown, & Co., Inc.; Boston, MA, pp. 13-24, 1997.

Grinstaff et al., "Air-filled proteinaceous microbubbles: synthesis of an echo-contrast agent", Proc. Natl. Acad. Sci. USA, 88:7708-7710, 1991.

Grubbs et al., " Ring-Closing Metathesis and Related Processes in Organic Synthesis", Acc. Chem. Res., 28:446-52, 1995.

Haes et al., "A nanoscale optical biosensor: sensitivity and selectivity of an approach based on the localized surface plasmon resonance spectroscopy of triangular silver nanoparticles", J. Am. Chem. Soc., 124:10596-604, 2002.

Handley et al., "Colloidal gold labeling studies related to vascular and endothelial function, hemostasis and receptor-mediated processing of plasma macromolecules", European J. Cell Biology, 43:163-74, 1987.

Handley et al., "Colloidal gold-low density lipoprotein conjugates as membrane receptor probes", Proc. Natl. Acad. Sci. USA, 78:368-71, 1981.

Handley "Methods for Synthesis of Colloidal Gold", Colloidal Gold: Principles, Methods, and Applications, (Academic Press), vol. 1, pp. 13-32, 1989.

Hardikar et al., "Coating of nanosize silver particles with silica", J. Colloid and Interface Science, 221:133-36, 2000.

Harrington et al., "Gene therapy for prostate cancer: current status and future prospects", J. Urology, 166:1220-33, 2001.

Hartl et al., "Ultrahigh-Resolution Optical Coherence Tomography Using Continuum Generation In An Air-Silica Microstructure Optical Fiber", Optics Letters, 26:608-610, 2001.

Hiergeist et al., "Application of magnetite ferrofluids for hyperthermia", J. Magnetism and Magnetic Materials, 201:420-22, 1999.

Hirsch et al., "A Whole Blood Immunoassay Using Gold Nanoshells", Analytical Chemistry, 75:2377-2381, 2003.

Jackson et al., "Silver Nanoshells:Variations in Morphologies and Optical Properties", J. Phys. Chem. B, 105:2743-46, 2001.

Jana et al., "Wet chemical synthesis of high aspect ratio cylindrical gold nanorods", J. Phys. Chem. B, 105:4065-67, 2001.

Jang et al., "Visualization of Coronary Atherosclerotic Plagues in Patients Using Optical Coherence Tomography: Comparison With Intravascular Ultrasound", J. American College of Cardiology, 39:604-609, 2002.

Jensen et al., "Electrodynamics of noble metal nanoparticles and nanoparticle clusters", J. Cluster Science, 10:295-317, 1999.

Jin et al., "Photoinduced conversion of silver nanospheres to nanoprisms", Science, 294:1901-03, 2001.

Jordan et al., "Magnetic fluid hyperthermia (MFH): Cancer treatment with AC magnetic field induced excitation of biocompatible superparamagnetic nanoparticles", Magnetism and Magnetic Materials., 201:413-19, 1999.

Jue et al., "Addition of sulfhydryl groups to *Escherichia coli* ribosomes by protein modification with 2-iminothiolane (methyl 4-mercaptobutyrimidate)", Biochemistry, 17:5399-5406, 1978.

Kempka et al., "Binding, uptake, and transcytosis of ligands for mannose-specific receptors in rat liver: an electron microscopic study", Experimental Cell Research,176, 38-48, 1988.

Keye et al., "Argon Laser Therapy of Endometriosis: A Review of 92 Consecutive Patients" Fertility and Sterility, 47:208-212, 1987.

Kim et al., "Hollow silica spheres of controlled size and porosity by sol-gel processing", J. Am. Ceram. Soc., 74:1987-1992, 1991.

Kim et al., "Photochemical synthesis of gold nanorods" J. Am. Chem. Soc., 124:14316-17, 2002.

Kim et al., "Self-Organization of Large Gold Nanoparticle Arrays", J. Am. Chem. Soc., 123:7955-56, 2001.

Kim et al., "Fabrication of hollow silica aerogel spheres by a droplet generation method and sol-gel processing" J. Vac. Sci., Technol. A., 7:1181-1184, 1989.

Kneipp et al., "Ultrasensitive Chemical Analysis by Raman Spectroscopy", Chem. Rev., 99:2957-75, 1999.

Kolb-Bachofen et al., "Electron microscopic evidence for an asialoglycoprotein receptor on Kupffer cells: localization of lectin-mediated endocytosis", Cell, 29:859-66, 1982.

Kolbeck, "The biomedical applications of protein microspheres", Ph.D. Doctoral Thesis, University of Illinois, Urbana-Champaign, title page and pp. 153, 159-160, 1999.

Korbelik et al., "Photofrin accumulation in malignant and host cell populations of various tumours", British Journal of Cancer, 73:506-513, 1996.

Langer "Drug delivery and targeting", Nature, 392:5-10, 1998.

Larson et al., "Water-Soluble Quantum Dots for Multiphoton Fluorescence Imaging in Vivo", Science, 300:1434-1436, 2003.

Lasic et al., "Liposomes revisited", Science, 267:1275-1276, 1995.

Lee et al., "Delivery of liposomes into cultured KB cells via folate receptor-mediated endocytosis", J. Biological Chemistry, 269:3198-3204, 1994.

Lee et al., "Engineered microsphere contrast agents for optical coherence tomography", Optics Letters, vol. 28, No. 17, pp. 1546-1548, 2003.

Lee et al., "Optical Characterization of Contrast Agents for Optical Coherence Tomography", Proceedings of SPIE, vol. 4967, pp. 129-134, 2003.

Leelarasamee et al., "A method for the preparation of polylactic acid microcapsules of controlled particle size and drug loading", J. Microencapsulation, 5:147-157, 1988.

Leitgeb et al., "Spectral measurement of absorption by spectroscopic frequency-domain optical coherence tomography", Optics Letters, 25:820-22, 2000.

Li et al., "Imaging Needle for Optical Coherence Tomography", Optics Letters, 25:1520-1522, 2000.

Li et al., "On the growth of highly ordered pores in anodized aluminum oxide", Chem. Mater., 10:2470-80, 1998.

Li et al., "Polycrystalline nanopore arrays with hexagonal ordering on aluminum", J. Vac. Sci. Technol. A, 17:1428-31, 1999.

Licha, "Contrast agents for optical imaging", Topics in Current Chemistry, 222:1-29, 2002.

Lin et al. "Measurement of tissue optical properties by the use of oblique-incidence optical fiber reflectometry", Applied Optics, 36:136-43, 1997.

Lin et al., "Intraocular Microsurgery with a Picosecond Nd:YAG Laser", Lasers in Surgery and Medicine, 15:44-53, 1994.

Liu et al., "In vivo measurement of oxygen concentration using sonochemically synthesized microspheres", Biophysical J., 67:896-901, 1994.

Liu et al., "A novel two-step silica-coating process for engineering magnetic nanocomposites", Chem. Mater., 10:3936-40, 1998.

Liz-Marzan et al., "Homogeneous silica coating of vitreophobic colloids", Chem. Commun., 731-32, 1996.

Lvov et al., "Nanoparticle/polyion assembly on microtemplates (lipid tubules and latex spheres)", Colloids and Surfaces B: Biointerfaces, 23:251-256, 2002.

Lvov et al., "Thin film nanofabrication via layer-by-layer adsorption of tubule halloysite, spherical silica, proteins and polycations", Colloids and Surfaces A: Physicohem. Eng. Aspects, 198-200:375-382, 2002.

Marks et al., Nonlinear interferometric vibrational imaging, E-print@arxiv.org/physics/0311071, URL http://www.arxiv.org/abs/physics/0311071, pp. 1-5, 2003.

Marks et al., "Study of an Ultrahigh-Numerical-Aperture Fiber Continuum Generation Source For Optical Coherence Tomography", Optics Letters, 27:2010-2012, 2002.

Marks et al., "Pulse shaping strategies for nonlinear interferometric vibrational imaging optimized for biomolecular imaging", Conference Proceeding: EMBC 2004: 26th Annual International Conference of the Engineering in Medicine and Biology Society (Sep. 1-5, 2004, San Francisco, CA), vol. 2, 7 pages, (accession No. 8255487).

Masuda et al., "Ordered metal nanohole arrays made by a two-step replication of honeycomb structures of anodic alumina", Science, 268:1466-68, 1995.

Mathias et al., "Tumor-selective radiopharmaceutical targeting via receptor-mediated endocytosis of Gallium-67-deferoxamine-folate", J. Of Nuclear Medicine, 37:1003-1008, 1996.

McNamara III et al., "Sonoluminescence temperatures during multibubble cavitation", Nature, 401:772-775,1999.

Micali et al., "Separation of Scattering and Absorption Contributions in UV/Visible Spectra of Resonant Systems", Anal. Chem., 73:4958-63, 2001.

Minton et al., "The Laser in Surgery. A 23 Year Perspective.", American Journal of Surgery, 151:725-729, 1986.

Mock et al., "Composite plasmon resonant nanowires", Nano Letters, 2:465-69, 2002.

Mock et al., "Shape effects in plasmon resonance of individual colloidal silver nanoparticles", J. Chem. Phys., 116:6755-59, 2002.

Mohwald, "From Langmuir monolayers to nanocapsules", Colloids and Surfaces A: Physicochem. Eng. Aspects, 171:25-31, 2000.

Morgner et al., "Spectrosopic optical coherence tomography", Optics Letters, 25:111-13, 2000.

Nicewarner-Peña et al. "Submicrometer metallic barcodes", Science, 294:137-41, 2001.

Nielsch et al., "Self-ordering regimes of porous alumina: the 10% porosity rule", Nano Letters 2:677-80, 2002.

Novak et al., "Purification of molecularly bridged metallic nanoparticle arrays by centrifugation and size exclusion chromatography", Anal. Chem., 73:5758-61, 2001.

Oldenburg et al., "Light Scattering From Dipole and Quadrupole Nanoshell Antennas", Appl. Phys. Lett., 75:1063-65, 1999.

Pasternack et al., "Resonance Light Scattering: A New Technique For Studying Chromophore Aggregation", Science, 269:935-39, 1995.

Pathak et al., "Detection of squamous neoplasia by fluorescence imaging comparing porfimer sodium fluorescence to tissue autofluorescence in the hamster cheek-pouch model", American Journal of Surgery, 170:423-426, 1995.

Peters, All about Albumin, in Biochemistry, Genetics, and Medical Applications, (Academic Press, New York), 3 pages, 1996.

Pinkerton et al., "Aerosolized fluorescent microspheres detected in the lung using confocal scanning laser microscopy", Microscopy Research and Technique, 26:437-443, 1993.

Pollack et al., "Circumferential Argon Laser Photocoagulation for Prevention of Retinal Detachment", Eye, vol. 8, pp. 419-422, 1994.

Prudhomme et al., "Interstitial Diode Laser Hyperthermia in the Treatment of Subcutaneous Tumor", Lasers in Surgery and Medicine, 19:445-450, 1996.

Puliafito et al., "Optical Coherence Tomography of Ocular Diseases", Slack Inc, Thorofare, N.J., pp. 3-34, 369-374, 1995.

Pusztay et al., "Encagement of Gold Nanoclusters in Crosslinked Resorcinarene Shells", Supramolecular Chemistry, 14:291-94, 2002.

Quaroni et al., "Preparation of Polymer-Coated Functionalized Silver Nanoparticles", J. Am. Chem. Soc., 121:10642-43, 1999.

Russell-Jones, "Use of vitamin $B_{12}$ conjugates to deliver protein drugs by the oral route", Critical Reviews in Therapuetic Drug Carrier Systems, vol. 15, No. 6, pp. 557-586, 1998.

Sadtler et al., "Spherical ensembles of gold nanopartides on silica: electrostatic and size effects", Chem. Commun., 1604-05, 2002.

Sansdrap et al., "Influence of manufacturing parameters on the size characteristics and the release profiles of nifedipine from poly(DL-lactide-co-glycolide) microspheres", International Journal of Pharmaceutics, 98:157-164, 1993.

Schaefer et al., "Real-Time Digital Signal Processing-Based Optical Coherence Tomography and Doppler Optical Coherence Tomography", IEEE Transactions on Biomedical Engineering, vol. 51, No. 1, pp. 186-190, 2004.

Schaefer "Real-Time, Digital Signal Processing-Based Optical Coherence Tomography and Optical Doppler Tomography", Master Thesis, University of Illinois at Urbana-Champaign, 2001.

Sevick-Muraca et al., "Fluorescence-enhanced, near infrared diagnostic imaging with contrast agents", Current Opinion in Chemical Biology, Op. Chem. Biol., 6:642-50, 2002.

Shiga et al., "Preparation of Poly(D,L-lactide) and Copoly(lactide-glycolide) Microspheres of Uniform Size", J. Pharm. Pharmacol., 48:891-895, 1996.

Shipway et al., "Nanoparticle arrays on surfaces for electronic, optical, and sensor applications", ChemPhysChem., 1:18-52, 2000.

Slaga et al., "An animal model for oral cancer", J. National Cancer Institute Monographs, 13:55-60, 1992.

Sokolov et al., "Real-Time Vital Optical Imaging of Precancer Using Anti-Epidermal Growth Factor Receptor Antibodies Conjugated to Gold Nanoparticles", Cancer Research, 63:1999-2004, 2003.

Sönnichsen et al., "Drastic reduction of plasmon damping in gold nanorods", Physical Review Letters, vol. 88, No. 7:077402-1 to 077402-4, 2002.

Sönnichsen et al., "Spectroscopy of Single Metallic Nanoparticles Using Total Internal Reflection Microscopy", Appl. Phys. Lett., 77:2949-51, 2000.

Stavens et al., "Encapsulation of Neutral Gold Nanoclusters by Resorcinarenes", Langmuir, 15:8337-39, 1999.

Su et al., "Tumor characterization with dynamic contrast-enhanced MRI using MR contrast agents of various molecular weights", Magnetic Resonance in Medicine, 39:259-269, 1998.

Suslick et al., "Protein Microencapsulation of Nonaqueous Liquids", J. Am. Chem. Soc., 112:7807-7809, 1990.

Suslick et al., "Versatile sonochemical reaction vessels" in Experimental Organometallic Chemistry: A Practicum in Synthesis and Characterization, (A. Wayda, Darensburg MY, eds. ACS Symposium Series, Washington, D.C.), pp. 195-197, 1987.

Suslick, "Sonochemistry", Science, 247: 1439-1445, 1990.

Tanaka et al., "Direct visualization of colloidal gold-bound molecules and a cell-surface receptor by ultrahigh-resolution scanning electron microscopy", J. Microscopy, 161:455-61, 1991.

Tearney et al., "Catheter-based optical imaging of a human coronary artery", Circulation, 94: 3013, 1996.

Tearney et al., "High-Speed Phase- and Group-Delay Scanning with a Grating-Based Phase Control Delay Line", Optics Letters, vol. 22, No. 23:1811-1813, 1997.

Toth et al., "Retinal effects of ultrashort laser pulses in the rabbit eye", Investigative Ophthalmology & Visual Science, 36:1910-17, 1995.

Toublan et al., "Magnetically-inducible optical contrast agents for optical coherence tomography", presented at the Optical Society of America Biomedical Topical Meeting, Miami, FL, Apr. 7-10, 2002.

Tripp et al., "Self-assembly of cobalt nanoparticle rings", J. Am. Chem. Soc., 124:7914-15,2002.

Turkevich et al., "A Study of the Nucleation and Growth Processes in the Synthesis of Colloidal Gold", Faraday Soc., 11:55-75, 1951.

Tuting, "The immunology of cutaneous DNA immunization", Current Opinion in Molecular Therapeutics, vol. 1, No. 2, pp. 216-225, 1999.

Ung et al., "Controlled method for silica coating of silver colloids. Influence of coating on the rate of chemical reactions", Langmuir, 14:3740-48, 1998.

van der Laan et al., "In vitro activity of novel antifolates against human squamous carcinoma cell lines of the head and neck with inherent resistance to methotrexate", Int. J. Cancer, 51:909-914, 1992.

Van Der Smissen et al., "Ligand-induced clustering of asialoglycoprotein receptors on rat hepatocytes at 4° C.", European J. of Cell Biology, 60:122-30, 1993.

Van Der Smissen et al., "Quantitative analysis of clustering on biological membranes: methodology and application to ligand-induced asialoglycoprotein receptor redistribution on rat hepatocytes", European J. of Cell Biology, 69:45-54, 1996.

van der Zande et al., "Colloidal dispersions of gold rods: synthesis and optical properties", Langmuir, 16:451-58, 2000.

Violante et al., "Improved detectability of VX2 carcinoma in the rabbit liver with contrast enhancement in computed tomography", Radiology, 134:237-239, 1980.

Vitkin et al., "Optical and thermal characterization of natural (*Sepia officinalis*) melanin", Photochemistry and Photobiology, 59:455-62, 1994.

Vo-Dinh, "Surface-Enhanced Raman Spectroscopy Using Metallic Nanostructures", Trends in Analytical Chemistry, 17:557-82, 1998.

Wang et al., "Semiconductor quantum dot-labeled microsphere bioconjugates prepared by stepwise self-assembly", Nano Lett., 2:857-861, 2002.

Xu et al., "Electromagnetic Contributions to Single-Molecule Sensitivity in Surface-Enhanced Raman Scattering", Physical Review E, 62:4318-24, 2000.

Yguerabide et al., "Light-scattering submicroscopic particles as highly fluorescent analogs and their use as tracer labels in clinical and biological applications", Analytical Biochemistry, 262:137-56, 1998.

Yu et al., "Gold nanorods: electrochemical synthesis and optical properties", J. Phys. Chem. B, 101:6661-64, 1997.

Volkmer et al., "Vibrational imaging with high sensitivity via epidected coherent anti-Stokes Raman scattering microscopy", Phys. Rev. Lett., 87(2):023901-1-4, 2001.

Invitation to pay additional fees and partial search report dated Apr. 4, 2008 for PCT application No. PCT/US2007/061364.

* cited by examiner

NONLINEAR INTERFEROMETRIC VIBRATIONAL IMAGING

CROSS REFERENCE TO RELATED APPLICATIONS

The present application claims priority to U.S. Provisional application 60/442,300, filed Jan. 24, 2003, which is hereby incorporated by reference.

FEDERALLY SPONSORED RESEARCH OR DEVELOPMENT

The subject matter of this application may in part have been funded by the NASA/National Cancer Institute (Contract no. NAS2-02057). The government may have certain rights in this invention.

BACKGROUND

The ability to measure the three-dimensional structure of biological tissues is important, but common methods used to leave out basic information about the molecular composition and metabolic behavior of the tissue imaged. This molecular composition and metabolic behavior information may yield valuable scientific data on the behavior of biological systems, and would be of great clinical diagnostic value for finding diseases such as cancer. Much of the focus of biological and medical imaging today is to gain information about composition.

Functional magnetic resonance imaging (FMRI) utilizes contrast agents specific to particular molecular species or metabolic processes to provide specific information about the three-dimensional (3-D) location of these species or processes. This method is quite versatile, and poses relatively little risk to the patient, but is limited in practice to a resolution over 100 microns. Positron Emission Tomography (PET) and Single Photon Emission Computed Tomography (SPECT) utilizes a radiolabeled metabolic molecule to provide 3-D measurements of utilization of these molecules by sensing their gamma-ray emissions. Unfortunately, these methods have been cost prohibitive as diagnostic tools, and expose the patient to ionizing radiation. Fluorescence microscopy labels relevant biological structures and processes with a fluorescent compound which can be measured by conventional microscopy or confocal microscopy. The two-photon variant uses ultrafast pulses so that emission and excitation frequencies can be clearly separated, and also utilizes the additional selectivity that the intensity-sensitive nature of two-photon excitation provides. While some biological structures produce natural fluorescence, in general externally introduced fluorescence markers must be used, which can interfere with biological processes and are often toxic.

Molecules frequently have molecular resonance frequencies that are due to the electromagnetic attractions of atoms in the molecule. These frequencies are those of molecular vibrations, molecular rotational motions, the excitation of electrons to higher energy states, and occasionally finer structures such as hyperfine interactions and optical-magnetic properties. These properties are present without the introduction of any external contrast molecule. These frequencies are usually in the mid-infrared, corresponding to photons of 1.5-50 microns of wavelength. Unfortunately, they cannot be directly excited by electromagnetic radiation of the same frequency because when they are in tissue, the surrounding water absorbs almost all of these frequencies. The range of wavelengths that the tissue is relatively transparent to is 0.6-1.5 microns. Therefore multiphoton nonlinear processes need to be employed to probe these resonances. The photons to stimulate and record the processes are typically in a region where the tissue is not absorbing, so that they can reach the tissue feature and be measured from the feature.

Raman spectroscopy, first discovered in 1928, uses molecular resonance features of frequency $\Delta\omega$ to split a photon of frequency $\omega$ into another photon of frequency $\omega-\Delta\omega$ and a resonance excitation of frequency $\Delta\omega$. The presence of photons at frequency $\omega-\Delta\omega$ identifies the concentration of the resonance feature. This process is in practice very weak and requires large amounts of power to produce any detectable amounts of photons. This weakness is due to the fact that the probability of a Raman excitation process to occur is proportional to the number of photons at frequency $\omega-\Delta\omega$ already present, of which there are typically few or none. Since photons that would be emitted by Raman excitation at frequency $\omega-\Delta\omega$ are indistinguishable from the incoming radiation that stimulates them, this is not a viable technique for achieving molecular sensitivity.

Coherent Anti-Stokes Raman Scattering (CARS) is another nonlinear spectroscopy technique that unlike conventional Raman spectroscopy, allows all of the photons necessary to stimulate the process to be introduced into the tissue by the illuminating source. This enables the probability of a CARS interaction to be increased to a (theoretically arbitrarily) high level so that a sufficient number of photons can be produced as to enable detection within a reasonable time period. It is essentially two stimulated Raman scattering processes in parallel. Two photons, a "pump" of frequency $\omega_1$ and a "Stokes" of frequency $\omega_2$ illuminate the tissue. They must be separated in frequency by $\omega_1-\omega_2=\Delta\omega$, which is the frequency of the molecular resonance. When molecules of the target molecular species are present, the resonance will be excited, and the pump photon will be converted to the same frequency as the Stokes photon. This is the first stimulated Raman scattering process. Another photon may arrive at frequency $\omega_3$ that will stimulate the emission of the excitation from the resonance, so that the energy of the photon of frequency $\omega_4$ and the excitation are converted to a new photon of frequency $\omega_4=\omega_3+\Delta\omega$, called the "anti-Stokes" photon. The presence of this photon of frequency $\omega_4$ indicates that a CARS process has taken place and indeed a molecule with the resonance feature is present. Often the "pump" beam is used as the photons of frequency $\omega_3$, so that $\omega_3=\omega_1$ and $\omega_4=2\omega_1-\omega_2$. Since the photon of $\omega_4$ is not the same frequency as one of the illuminating photons, and is typically within the transparency range of the tissue, it is easily discriminated from the incoming radiation. FIG. 1A shows an energy-level diagram for CARS, and FIG. 1B shows an energy-level diagram for Coherent Stokes Raman Scattering.

CARS microscopy uses the CARS process to look for the presence of a molecular species, but does not require any foreign substances to be introduced into the tissue. It scans the illumination point-by-point through the tissue and measures the number of generated anti-Stokes photons. When a three-dimensional mesh of points has been scanned, a complete three-dimensional picture of molecules of that resonance can be shown. Since CARS is a nonlinear process (and therefore is intensity sensitive), efficient conversion only occurs at the focus of the illumination, which can be made very tight (typically a half micron in both the axial and lateral directions). Therefore the resolution can be made many orders of magnitude better than MRI, which is the probably the largest competition for clinical use for similar purposes. Unfortunately, the penetration is usually rather low (limited to about 500 microns). A further shortcoming is that CARS microscopy measures the total number of anti-Stokes photons, or power, from the sample. However, the optical field contains temporal structure in the phase that is averaged out by power detection because photodetector response time is orders of magnitude slower than the oscillations of the optical field. The time scale on which the optical pulse varies (which is typically picoseconds or femtosecond time scales) is far too fast for photon detection equipment or electronics to detect (the fastest of which may detect 25 ps time scales).

Optical coherence tomography (OCT) is an emerging high-resolution medical and biological imaging technology [15-21]. OCT is analogous to ultrasound B-mode imaging except reflections of low-coherence light are detected rather than sound. OCT detects changes in the backscattered amplitude and phase of light.

Cross-sectional OCT imaging is performed by measuring the backscattered intensity of light from structures in tissue. This imaging technique is attractive for medical imaging because it permits the imaging of tissue microstructure in situ, yielding micron-scale imaging resolution without the need for excision and histological processing. Because OCT performs imaging using light, it has a one- to two-order-of-magnitude higher spatial resolution than ultrasound and does not require contact with tissue.

OCT was originally developed and demonstrated in ophthalmology for high-resolution tomographic imaging of the retina and anterior eye [22-24]. Because the eye is transparent and is easily optically accessible, it is well-suited for diagnostic OCT imaging. OCT is promising for the diagnosis of retinal disease because it can provide images of retinal pathology with 10 μm resolution, almost one order-of-magnitude higher than previously possible using ultrasound. Clinical studies have been performed to assess the application of OCT for a number of macular diseases [23,24]. OCT is especially promising for the diagnosis and monitoring of glaucoma and macular edema associated with diabetic retinopathy because it permits the quantitative measurement of changes in the retinal or retinal nerve fiber layer thickness. Because morphological changes often occur before the onset of physical symptoms, OCT can provide a powerful approach for the early detection of these diseases.

Recently, OCT has been applied for imaging a wide range of nontransparent tissues [16,17,25-27]. In tissues other than the eye, the imaging depth is limited by optical attenuation due to scattering and absorption. A "biological window" exists in tissue where absorption of near-infrared wavelengths is at a minimum and light can penetrate deep into highly-scattering tissue (FIG. 15) [28]. Because optical scattering decreases with increasing wavelength, OCT in nontransparent tissues has routinely used 1.3 μm wavelength light for imaging. In most tissues, imaging depths of 2-3 mm can be achieved using a system detection sensitivity of 110 dB (1 part in $10^{11}$). OCT has been applied to image arterial pathology in vitro and has been shown to differentiate plaque morphology with superior resolution to ultrasound [17,29].

Imaging studies have also been performed to investigate applications in gastroenterology, urology, and neurosurgery [30-32]. High resolution OCT using short coherence length, short-pulse light sources, has also been demonstrated and axial resolutions of less than 5 μm have been achieved [33, 34]. High-speed OCT at image acquisition rates of 4 to 8 frames per second for 500 to 250 square pixel images has been achieved [35]. OCT has been extended to perform Doppler imaging of blood flow and birefringence imaging to investigate laser intervention [36-38]. Different imaging delivery systems including transverse imaging catheters and endoscopes, and forward imaging devices have been developed to enable internal body OCT imaging [39,40]. Most recently, OCT has been combined with catheter-endoscope-based delivery to perform in vivo imaging in animal models and human patients [41-44].

Apart from medical applications, OCT has been demonstrated as an emerging investigational tool for cell and developmental biology. OCT has imaged the development of numerous animal models including *Rana pipiens* and *Xenopus laevis* (Leopard and African frog), and *Brachydanio rerio* (zebrafish) [45-46]. High-speed OCT imaging has permitted the morphological and functional imaging of the developing *Xenopus* cardiovascular system, including changes in heart function following pharmacological interventions [47]. High-resolution imaging has permitted the real-time tracking of cell dynamics in living specimens including mesenchymal cell mitosis and neural crest cell migration [48]. OCT is advantageous in microscopy applications because repeated non-invasive imaging of the morphological and functional changes in genetically modified animals can be performed overtime without having to histologically process multiple specimens. The high-resolution, cellular-imaging capabilities suggest that OCT can be used to diagnose and monitor early neoplastic changes in humans.

The ability of OCT to perform optical biopsies, the in situ imaging of tissue microstructure at near-histological resolution, has been used to image morphological differences between normal and neoplastic tissue. OCT images of in vitro neoplasms of the female reproductive tract [49], the gastrointestinal tract [50], and the brain [51] have been investigated. Optical differences between normal and neoplastic tissue were evident, but primarily for late-stage changes. Still, situations exists were no inherent optical contrast exists between normal and pathologic tissue, such as in early-stage, pre-malignant tumors or in tumors which remain optically similar to normal tissue.

In the past, OCT has found numerous medical and biological applications. However, the imaging technique has relied largely on the inherent optical properties of the tissue to provide contrast and differentiate normal from pathological tissue. Phospholipid-coated perfluorobutane microbubbles (ImaRx Pharmaceutical, Tucson, Ariz.) have been used as a contrast agent for OCT; although they produce a strong OCT signal, blood and tissue also produce a fairly strong OCT signal, and the effects of this contrast agent in vivo on the visualization of blood vessels are subtle.

SUMMARY OF THE INVENTION

In a first embodiment, the invention provides a method of examining a sample, which includes: exposing a reference to a first set of electromagnetic radiation, to form a second set of electromagnetic radiation scattered from the reference; exposing a sample to a third set of electromagnetic radiation to form a fourth set of electromagnetic radiation scattered from the sample; and interfering the second set of electromagnetic radiation and the fourth set of electromagnetic radiation. In this embodiment, the first set and the third set of electromagnetic radiation are generated from a source. Moreover, at least a portion of the second set of electromagnetic radiation is of a frequency different from that of the first set of electromagnetic radiation, and at least a portion of the fourth set of electromagnetic radiation is of a frequency different from that of the third set of electromagnetic radiation.

In a second embodiment, the invention provides a method of forming an image of a sample, which includes: exposing a reference to a first set of electromagnetic radiation, to form a second set of electromagnetic radiation scattered from the reference; exposing a sample to a third set of electromagnetic radiation to form a fourth set of electromagnetic radiation scattered from the sample; forming a digital data set corresponding to the sample; and converting the data set into an image. In this embodiment, the data set is formed by interfering the second set of electromagnetic radiation and the fourth set of electromagnetic radiation. Also, the first set and the third set of electromagnetic radiation are generated from a source. Moreover, at least a portion of the second set of electromagnetic radiation is of a frequency different from that of the first set of electromagnetic radiation, and at least a portion of the fourth set of electromagnetic radiation is of a frequency different from that of the third set of electromagnetic radiation.

In a third embodiment, the invention provides a device for examining of a sample having an oscillator, a reference generator that is optically coupled to the oscillator, a microscope that is optically coupled to the oscillator, a demodulator that is optically coupled to the reference generator and the microscope, and a recorder that is coupled to the demodulator.

In a fourth embodiment, the invention provides a method of examining a sample that includes exposing a sample to a first set of electromagnetic radiation to form a second set of electromagnetic radiation scattered from the sample, and interfering the second set of electromagnetic radiation with a third set of electromagnetic radiation. In this embodiment, the third set of electromagnetic radiation is phase-coherent with the first set of electromagnetic radiation, at least a first portion of the second set of electromagnetic radiation is of a frequency different from that of the first set of electromagnetic radiation, and at least a portion of the third set of electromagnetic radiation is of the same frequency as the first portion of the second set of electromagnetic radiation.

In a fifth embodiment, the invention provides a method of forming an image of a sample that includes exposing a sample to a first set of electromagnetic radiation to form a second set of electromagnetic radiation scattered from the sample, forming a digital data set corresponding to the sample, and converting the data set into an image. In this embodiment, the forming of the image includes interfering the second set of electromagnetic radiation and a third set of electromagnetic radiation. Moreover, the third set of electromagnetic radiation is phase-coherent with the first set of electromagnetic radiation. In addition, at least a first portion of the second set of electromagnetic radiation is of a frequency different from that of the first set of electromagnetic radiation, and at least a portion of the third set of electromagnetic radiation is of the same frequency as the first portion of the second set of electromagnetic radiation.

DETAILED DESCRIPTION

Figure 1:
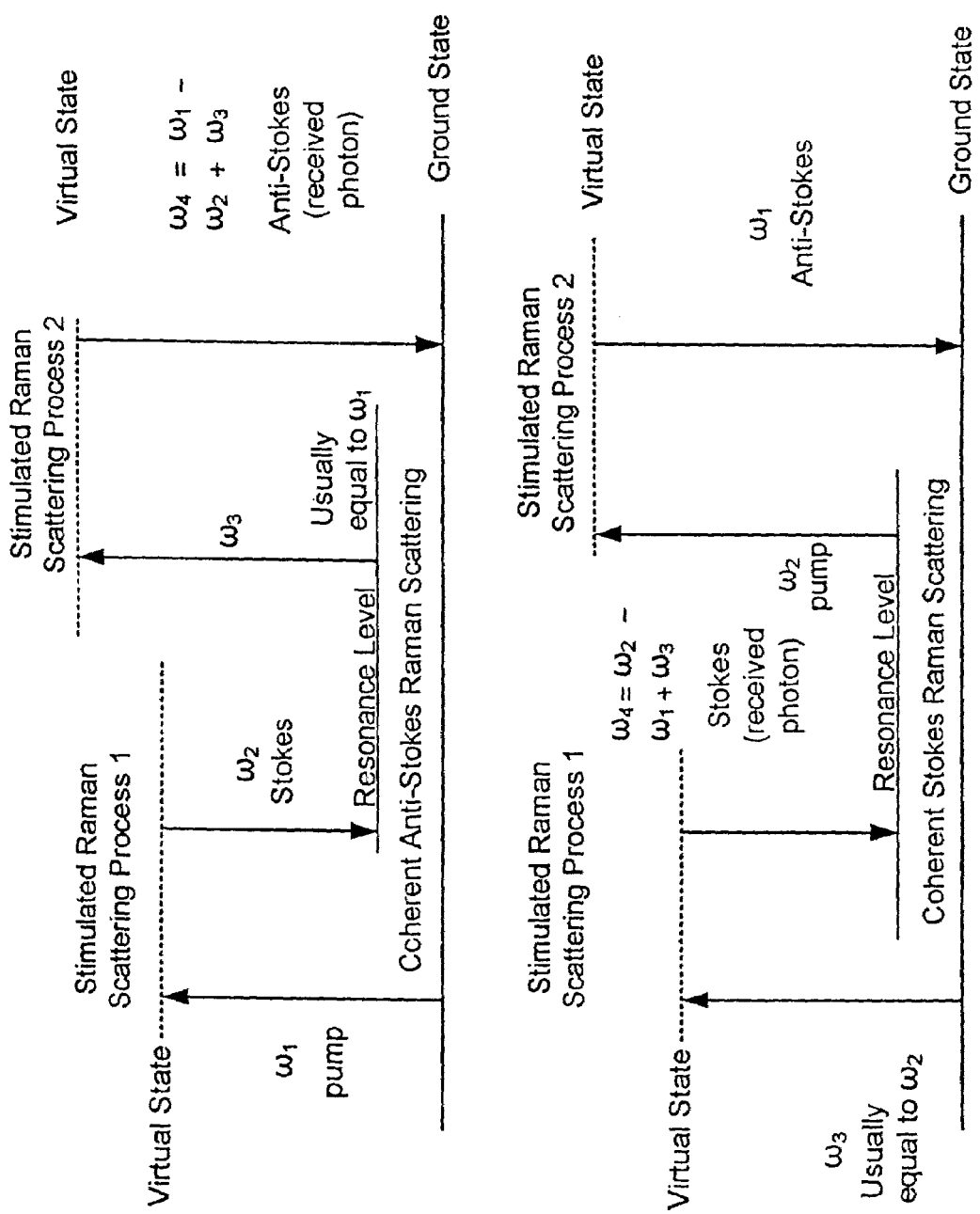
FIG. 1. Coherent Anti-Stokes Raman Scattering and Coherent Stokes Raman Scattering energy-level diagrams.

Nonlinear interferometric vibrational imaging (NIVI) is a method used to measure the three-dimensional distribution of molecular species in various samples (biological or otherwise). Its basic operation is to stimulate the excitation of molecular bonds with particular resonance frequencies, and then use these excitations to produce radiation distinct from the excitation that can be measured. The physical process of excitation and stimulation of radiation is called Coherent Anti-Stokes Raman Scattering (CARS). Unlike previous methods that use CARS in microscopy to probe for the presence of molecular species, NIVI utilizes a heterodyne approach where a reference signal is separately generated and interferomerically compared to the signal received from the sample, allowing the signal to be formed into an image in the same way as OCT. In this way, additional information can be inferred from the emitted radiation such as the distance to the sample and phase information that yields additional structure of the molecular bonds. It also has other advantages in sensitivity and the ability to screen out background radiation that is not produced by the sample. It also can allow more flexibility in the choice of laser illumination source, because the coherent detection process does not rely on photon frequency alone to discriminate emitted radiation.

The term "scattered photon" means photons scattered by a sample, which include linearly scattered photons and non-linearly scattered photons, such as CARS and CSRS photons.

The term "image" means data produced by receipt of electromagnetic radiation, which may or may not be formed into a picture viewable by the human eye. This includes images produced directly onto a medium such as film or video.

The phrase "frequency range of infra-red to ultraviolet" means electromagnetic radiation having a frequency of $10^{12}$ to $10^{17}$ Hz, which excludes radio waves, microwaves, X-rays and gamma rays. The term "light" means visible light.

The method of NIVI was developed at first because CARS microscopy based on non-interferometric detection is incompatible with the scanning modes of OCT. When the method of CARS microscopy is employed, information about the echo time of the optical signal is lost because the photodetector is not nearly fast enough to respond to the relatively instantaneous return of the return pulse. In OCT a reference wave is used so that the relative time delay between the reference wave and the returned echo wave can be determined. Nonlinear methods (such as conventional Raman spectroscopy) are unsuited to integration with OCT because the emitted signal is incoherent with respect to the excitation. However, CARS processes preserve coherence, and therefore enable interferometric methods to be used. By using a nonlinearly generated reference wave, the time of arrival of a CARS signal returning from the tissue can be interferometrically compared to the arrival time of the reference signal. In this way, the methods of OCT and CARS imaging can be integrated. In addition, in a manner analogous to how OCT can measure the dispersion of scatterers in the medium, NIVI can measure the dispersion of the response of molecules to the excitation radiation. This is because NIVI measures the relative phase between the reference signal and the sample signal. This dispersion should contain information about the resonance structure of the molecule over and above what can be measured using CARS microscopy.

The Nonlinear Interferometric Vibrational Imaging Method

Figure 2:
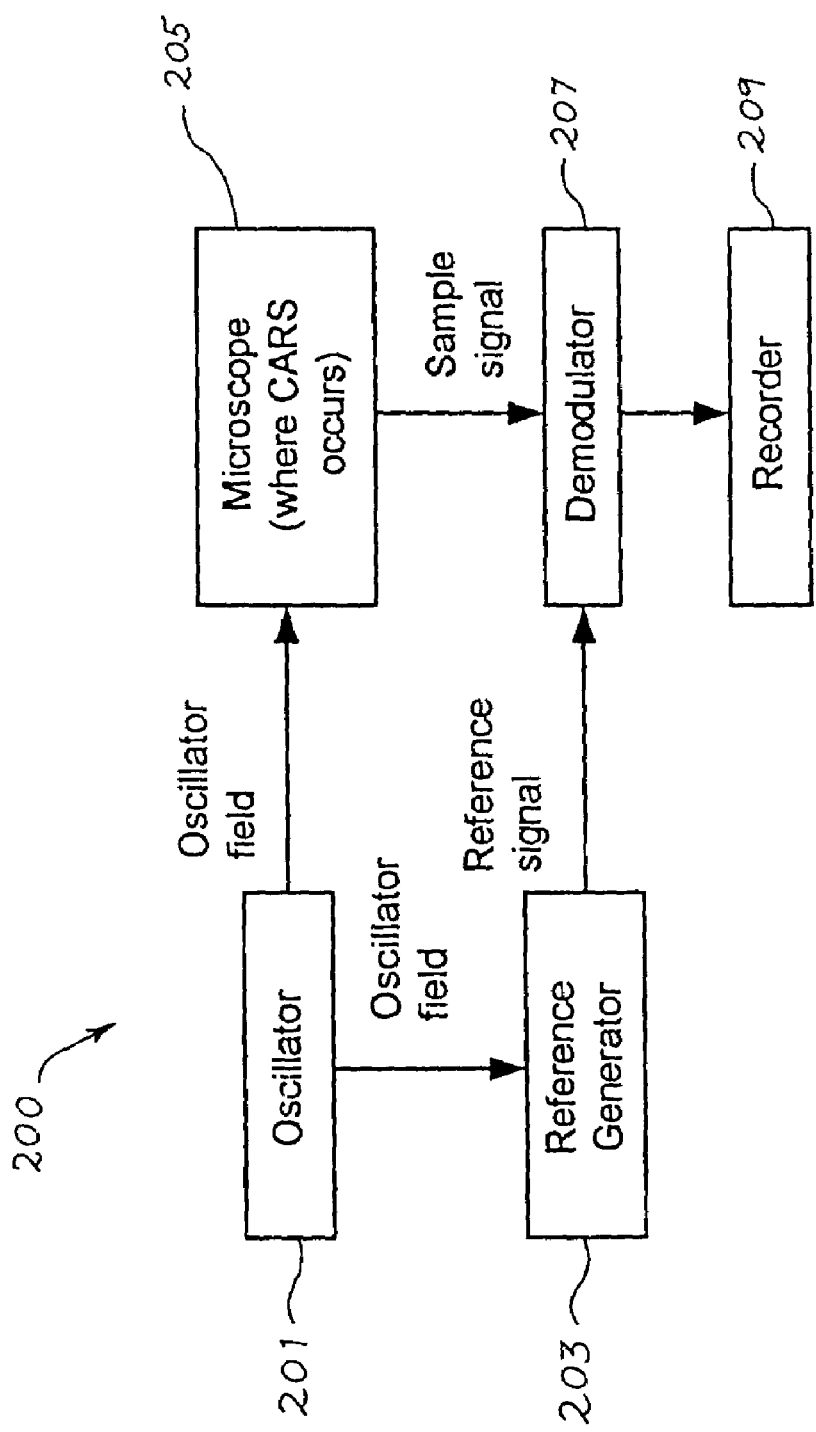
FIG. 2. Basic block diagram of NIVI

The purpose of NIVI is to measure the temporal field radiated by samples that are stimulated using the CARS technique. When the field is scanned through the sample, an image can be formed of the molecular contents of the sample. As illustrated in FIG. 2, a preferred embodiment NIVI 200 has the following components:

Oscillator. This oscillator 201 produces an optical field that can excite the resonance mode of the target molecule through a nonlinear technique (usually stimulated Raman scattering), and also the photon to stimulate the photon that is measured (also usually through stimulated Raman scattering). The combination of these processes is called CARS.

Reference Generator. The reference signal generator 203, which can sometimes be incorporated into the oscillator, converts part of the oscillator signal to a reference signal that can be used in the demodulator section. It acts as a known signal that demodulates the unknown signal from the sample in the interferometer.

Microscope. The microscope 205 delivers the field produced by the oscillator to the sample, and collects the field emitted by the sample. The excitation field is usually delivered by a microscope objective, where the oscillator field is focused tightly or sparsely, depending on the scanning method. This focus is scanned through the tissue, and based on the signal received from each tissue volume an image can be formed. When the oscillator signal is delivered to the tissue containing a molecule with a compatible resonance, a nonlinear process such as CARS can occur and produce a new sample signal (called the "anti-Stokes" for CARS processes). This sample signal serves as an indicator of the presence of the molecular resonance, and also provides additional information about the molecule through the temporal structure of the sample signal.

Demodulator. The demodulator 207 combines the signal received from the sample with the reference signal. This is typically achieved by constructing an interferometric crosscorrelator. The cross-correlation of the two signals is then measured by a single photodetector or array of photodetectors. The power received by these photodetectors allows the cross-correlation signal to be inferred, from which the temporal response signal from the sample can be also inferred. With knowledge of the physics of the molecule, the presence of and potentially properties of the molecule being tested can be inferred from its temporal response.

Recorder. The data recorder 209 records the data measured by the demodulator. This data can be digitally processed to produce an image that a human operator can interpret.

Each of these modules can be implemented in a variety of different ways that can be tailored to various data acquisition needs. In addition, while these units are the basic units of the invention, often the parts can be consolidated to simplify implementation or reduce cost. While the basic block design could be construed as that of a standard interferometric microscope, nonlinear processes are occurring in the reference generator and "Microscope" sections that allow the resonance information of the sample to be pumped.

Each of these units will be detailed presently.

1. Oscillator.

The oscillator produces the electromagnetic field that stimulates the excitation of the resonance to be probed. It also provides the photon that stimulates the output photon that is detected as evidence of CARS or CSRS. There are many types of oscillators and fields that can produce CARS. Each pulse produced by the oscillator should be nearly identical so that it can excite consistent signals in the reference generator and sample. If the oscillator produces too variable of a signal, the signals from the reference generator and sample may change and produce signals that can be confused with noise sources. Variability in the oscillator output is a noise source in itself that adds uncertainty to what the expected demodulated signal should be.

The conventional way to produce CARS is to send in two overlapped optical pulses, one of which at frequency $\omega_1$, the pump, and the other at $\omega_2$, the Stokes pulse, where $\omega_1 - \omega_2 = \Delta\omega$, where $\Delta\omega$ is the resonance frequency of the molecules of interest. These pulses produce a beat frequency of $\Delta\omega$ that manifests itself in the magnitude of the optical field. In linear time-independent optics, systems are sensitive only to the frequencies of the optical pulses themselves, and not any beats they may produce together. However, with sufficient intensity the intensity envelope may itself stimulate the molecule. By choosing two pulses that produce beats of this frequency, we can stimulate the molecule with two wavelengths that the tissue is transparent to. Once the resonance is stimulated, another photon of frequency $\omega_1$ (in CARS), or of frequency $\omega_2$ (in CSRS) stimulates the emission of a fourth photon, which is of frequency $2\omega_1 - \omega_2$ for CARS, and $2\omega_2 - \omega_1$ for CSRS.

Figure 3:
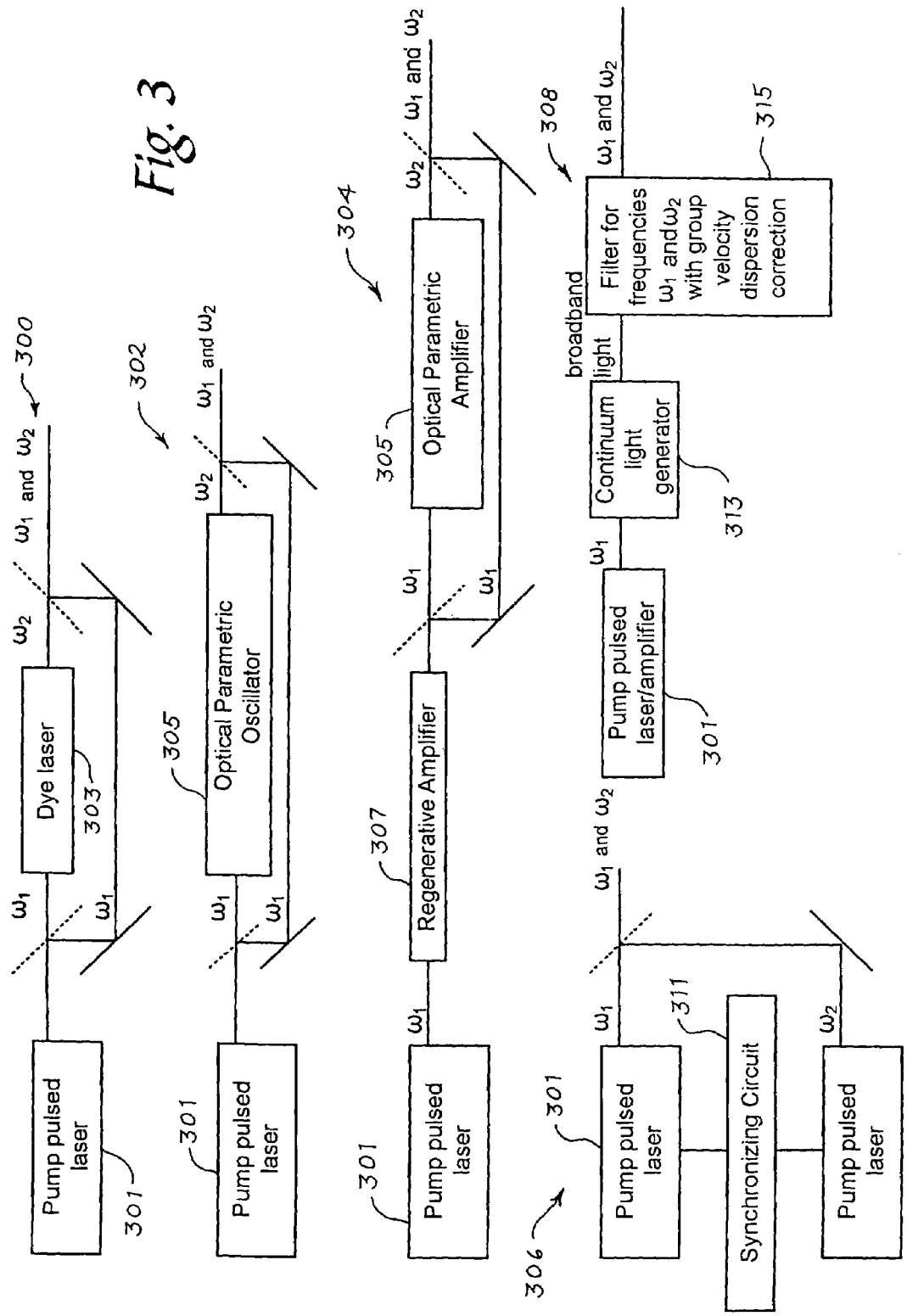
FIG. 3. Example laser configurations are shown that produce two pulses of frequencies $\omega_1$ and $\omega_2$ overlapped. We assume that the delays have been set correctly to overlap them.

Systems that can be used to produce these two frequencies are shown below in FIG. 3. A common configuration to produce pulses of these two wavelengths that are overlapped in time is to have a pulsed laser produce one of these wavelengths, split off of some of its energy, and use this energy to produce a second pulse of a lower or higher frequency. In one configuration 300, a pump laser 301 pumps a dye laser 303, for example a doubled Nd:YAG pump laser at 532 nm pumping a tunable dye laser. In another possible configuration 302, a pump laser such as a Ti-sapphire oscillator pumps an optical parametric oscillator (a device that converts pulses to lower frequencies) 305.

In yet another configuration 304, the pump laser pumps a regenerative amplifier 307, such as a Ti-sapphire regenerative amplifier. The regenerative amplifier then pumps an optical parametric amplifier (another frequency conversion device) 309. Alternatively, as illustrated in configuration 306, the pulses of each wavelength are generated by two separate pump lasers, and the time overlap is maintained by a circuit 311 that synchronizes the two sources. In another configuration 308, the pump laser pumps a continuum light generator 313, generating broadband light which is filtered by a filter for the two wavelengths with group velocity dispersion correction 315.

While directly generating the two frequencies and superimposing them to produce beats is the most common way to stimulate CARS, this method has some disadvantages for the method of NIVI. In CARS and CSRS, there are two types of generated signals. Resonant signals depend on the presence of a molecule of a particular resonance frequency to be present to generate the CARS signal. Another component, nonresonant CARS, does not require a particular frequency to perform conversion. Nonresonant CARS depends on the peak intensity in the signal, while the resonant component can build up from many beat periods and so therefore can be spread out in time. Because of this, it is advantageous to spread the CARS signals in time to reduce the nonresonant component.

However, when the two signals are discretely generated and are transform-limited (are not chirped in time), the only way to broaden the signals in time is to reduce their bandwidth. To achieve sufficient power-spectral-density to cause efficient conversion, the pulses must either generated by a low-bandwidth laser, or much power will be wasted in filtering a higher bandwidth signal. Unfortunately, the range resolution in OCT, when temporal ranging is used, is inversely proportional to the illumination bandwidth. This requirement for high bandwidth conflicts with the requirement for small bandwidth for resonance specificity. It would be desirable to come up with an alternate oscillator configuration that would preserve the resonance specificity of the low bandwidth pulses, but actually utilize high bandwidth signals.

Since the nonlinear excitation of the resonant molecule depends more on the beats produced than on the bandwidth used to produce them, it would be desirable to take a broadband pulse and reshape it into a signal with the required beat frequency. Recent advancements have made pulsed sources of very large bandwidth. Some of the methods to do this are high-bandwidth Ti-sapphire oscillators, dispersion compensated mirror Ti-sapphire oscillators, double chirped-mirror Ti-sapphire oscillators, and continuum generation sources. The optical field produced by these sources can be shaped into a field with the beats at the required frequency.

Figure 4:
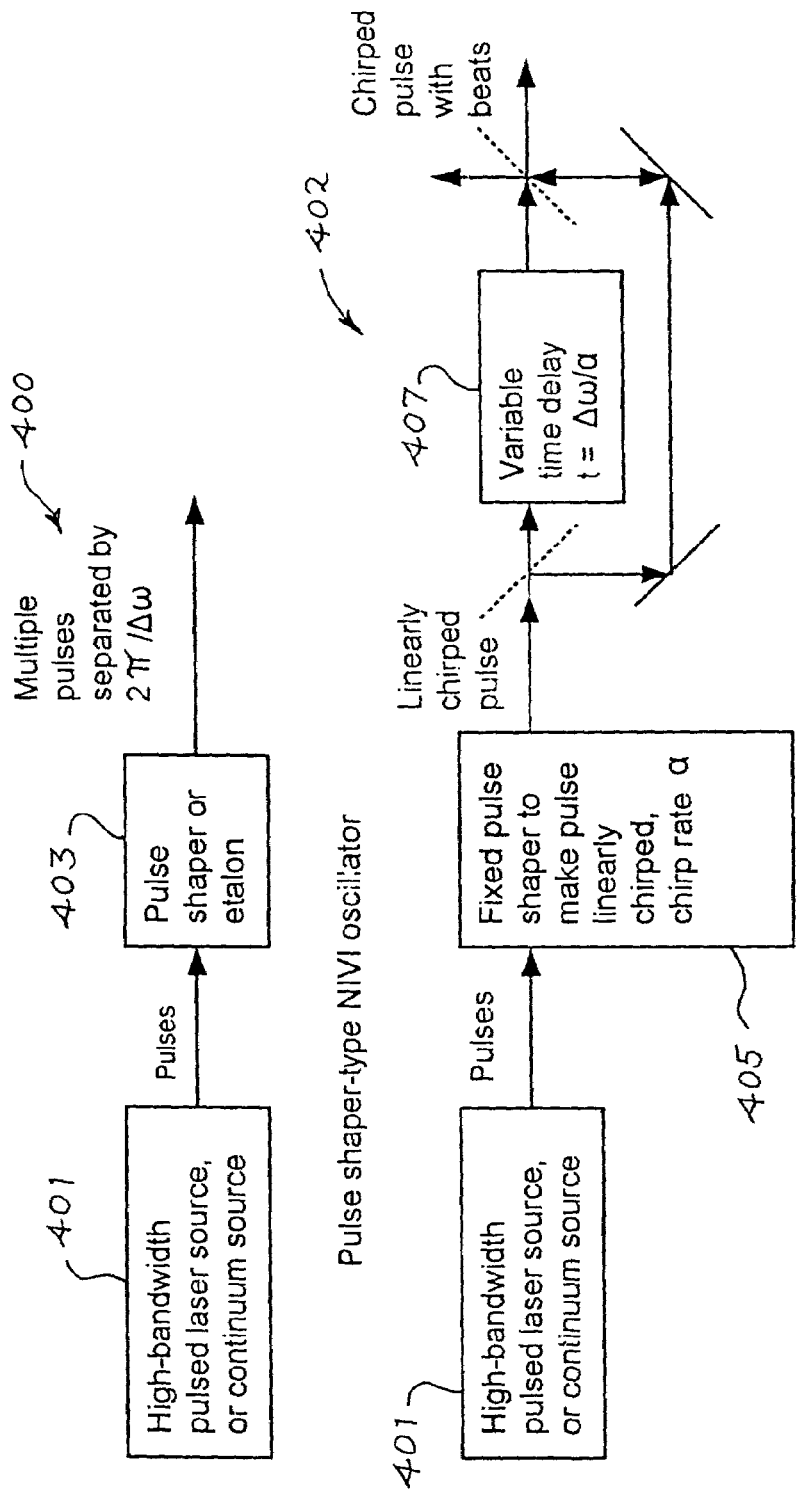
FIG. 4. Methods of shaping a broadband pulse into a pulse with beat frequency $\Delta\omega$.

One such method that has been demonstrated in the literature is shown in FIG. 4. A source of laser pulses from a laser source 401 is sent into a Fourier-plane pulse shaper 403 that utilizes a spatial-light-modulator (e.g. liquid crystal modulator or acousto-optic modulator). The Fourier-plane pulse shaper enables each frequency in the pulse to have its phase and/or amplitude altered. By applying the correct phase and amplitude to each incoming frequency, the incoming signal can be convolved with an essentially arbitrary signal. The pulse shaper is set up to reshape the incoming pulse by applying a period phase or amplitude perturbation in the Fourier domain with period $\Delta\omega/N$, where N is a positive integer. This will transform a single pulse into a train of pulses that are separated in time by $2\pi/\Delta\omega$. If only a phase perturbation is used, the power of the signal can be maximally preserved. The larger the integer N is, the longer the pulse train will be, and none of the bandwidth of the original pulse will be lost. However, most pulse shapers have a limited number of controllable frequencies, limiting the practical size of N.

One advantage of spatial-light-modulator based pulse shapers is that there is typically a wide range of pulse shapes that can be achieved, and the spatial-light-modulator can often be controlled automatically by a computer. The computer can then adjust the spatial-light-modulator to achieve maximum signal from the sample in a feedback loop. This may allow automatic correction of dispersion or aberrations introduced by the optics of the system, and will permit more flexibility in probing the molecule because of the tunability of the pulse shapes.

The pulse-shaper in the "Pulse-shaper type NIVI oscillator" 400 is well described in the literature. It consists of two diffraction gratings, which disperse and recombine the frequencies, two lenses that focus each frequency to a point and recollimate each frequency, and a pulse shaper placed at the focal plane to separately operate on each frequency. The pulse shape is altered by dispersing each frequency to a separate angle, and then imaging each frequency to a separate point on the spatial-light-modulator. Alternatively, an etalon may be used to shape the amplitude of the pulse periodically. Unfortunately, while this would be simpler, it modifies the spectrum of the pulse and therefore introduces artifacts into the NIVI image.

An alternative method is to take a pulse and impart a linear chirp to it. A linear chirp turns a pulse into one where the frequency rises or falls at a linear rate as a function of time. This rate is characterized by a constant $\alpha$, which is the change in frequency per unit time. It is called "chirped" because of the noise of the equivalent sound wave. If two copies of the chirped pulse are created, delayed with respect to each other by imparting a variable time delay 407, and recombined, the resulting pulse will have two simultaneous frequencies that will rise or fall together at the same linear rate, but always be separated at a given instant by the same frequency. If this separation frequency is chosen to be $\Delta\omega$, then the envelope of the pulse will be modulated by beats of this frequency. This method is especially convenient because the probed resonance frequency can be adjusted easily by adjusting the time delay between the two chirped pulses, which is relatively easy and inexpensive. This will enable a NIVI instrument that can be rapidly and easily adjusted to scan a wide range of molecular resonances. Systems based on tunable frequency sources will likely be much more difficult to dynamically change reliably and often.

The ability to linearly chirp a pulse is well known in the literature. It can be accomplished with a pulse shaper 405 having a combination of prisms, diffraction gratings, lenses, mirrors, and/or dispersive materials. Combinations may be required to ensure that the resulting chirp is linear and does not contain significant amounts of higher-order dispersion. Higher-order dispersion would limit the resolution to which the resonance could be addressed and exclude other nearby frequency resonances. In a typical Chirped CARS NIVI setup 402, the chirp rate required would be fixed and the chirp rate should need little or no adjustment in the field. Measuring devices such as Frequency Resolved Optical Gating can test whether a chirped pulse is linearly chirped.

When using high-bandwidth excitation for CARS, it is important to filter out the entire bandwidth of excitation before detection so it does not interfere with detection of the emitted anti-Stokes light (Stokes for CSRS), because the nonlinear emission can not be easily distinguished from the much larger linearly scattered excitation light. However, this linearly scattered light contains the same structure that conventional OCT imaging does, and may be used to measure this information at the same time that a NIVI image is recorded. This will be convenient for superimposing OCT and NIVI data onto the same image, because the acquisition of both types of data can be designed into the same instrument. This can be implemented in practice by using a dichroic beamsplitter to separate the excitation and response radiation, and measuring the cross-correlation of the two frequency bands separately using a cross-correlation demodulator.

With high-bandwidth sources where the entire bandwidth need not be utilized to produce the excitation field, it is possible to use the upper end (for anti-Stokes) or lower end (for Stokes) of this bandwidth as a reference field, eliminating the need to separately generate a reference field. However, the frequencies of the reference must occupy the same band as the received CARS/CSRS light from the sample. Some sources, especially continuum generation sources, will likely generate much more bandwidth than needed for pulse shaping and therefore will probably have this extra bandwidth available for this use. While a different process from CARS/CSRS typically generates this light, it will likely remain phase-coherent with the CARS/CSRS light and therefore should be useful as a reference. Phase-coherence depends on the mechanism of pulse/continuum generation and therefore its phase-coherence stability properties of a particular source type must be established before it is suitable for this purpose. A dichroic beamsplitter may be used to separate the frequency band corresponding to the response radiation from the oscillator energy, so that it may be utilized as a reference signal.

It is also possible to simultaneously stimulate the excitation of several resonances if the sample is illuminated with the appropriate pump and Stokes/anti-Stokes beams. For example, in CARS a narrowband pump signal and a wideband Stokes can be used to address many resonances simultaneously. This is called multiplex CARS and can be extended to CSRS with a broad anti-Stokes wavelength range. This may be used to measure the presence of several molecular resonances simultaneously in the sample. In addition, if several excitations can be produced in the same molecule simultaneously, the molecule will evolve to various quantum states depending on the relative amplitude and timing between the CARS/CSRS stimulating signals for each resonance. This may be produced by sending in multiple pairs of Stokes/anti-Stokes wavelengths and pump beams in with varying time delays between them. By varying the time delay between excitations, the molecule can be made to prefer Stokes or anti-Stokes emissions from a particular quantum state. This way, the amount of anti-Stokes radiation generated from each quantum state could be potentially probed to identify the molecule.

In general, the spatial-light-modulator system of FIG. 4 could be used to produce more general pulse shapes than a series of beats at a single resonance frequency. By using a more complicated pulse shape, several bonds present in a molecule can be coherently excited, and energy transferred between them in a coherent fashion. Because each molecule has some difference between the bonds presents and their relative orientation (and therefore the coupling in the quantum wave functions between them), pulses can be shaped that will selectively transfer energy between the states for a particular molecule, and not be selective for other similar molecules. In this way, the emission of stimulated Raman scattering or another coherent scattering process can be made more specific than just every molecule possessing a bond of a particular energy. With an automatically controlled pulse shaper, such as those based on spatial light modulators, feedback can be employed where the computer can test various pulse shapes, measure the resulting emitted light temporal signal using the demodulator, and progressive reshape the pulse to optimize the signal from the target molecule and exclude other molecules. Once a useful temporal field shape for stimulating a molecule has been found, it can be stored in a database and later used for identifying that molecule in the future.

2. Reference Generator.

The reference generator takes a portion of the signal produced by the oscillator and converts it to a reference signal. This reference signal is later used to demodulate the sample signal. The reference generator is a nonlinear process that converts light in the illumination bandwidth to light in the sample's emission bandwidth, so that interference can occur between them. This nonlinear process may or may not be CARS or CSRS.

A common implementation of the Reference Generator would be to focus the oscillator excitation into a sample of the same molecular species that one wishes to image. The reference signal should then be very similar to the same molecular species contained in the sample. This is because they are the same molecule, illuminated by nearly identical pulses, converting them to the output signal using resonant CARS or CSRS. The magnitude of the cross-correlation between these two signals should be great because of their similarity. In addition, if there is variability of oscillator output, having the reference generator and sample contain the same substance will respond in similar ways, so that the cross-correlation signal can remain high despite fluctuations in the oscillator. The benefit of using the same molecule in the reference generator is that it is the molecule's signal that acts as its own "fingerprint" with which the cross-correlation can use to recognize the molecule in the sample. If more selective excitation processes than CARS are used, then using the same molecule in both reference and sample will help ensure that a reference signal can be generated for a given excitation field.

A nonresonant nonlinearity can be used as the reference generator as long as the peak power of the oscillator signal can excite a sufficient quantity of reference signal. High peak power can be maintained by not chirping the oscillator signal that is sent to the reference generator, while sending a relatively low peak power signal to the sample. Nonresonant CARS or CSRS can be used to generate an anti-Stokes or Stokes signal, respectively, from a medium that does not necessarily have a resonance at the frequency of the target molecule. The benefit of this is that the medium may not have to be changed each time a different molecular species is scanned for, because otherwise a medium with a resonance at that wavelength would need to be chosen. Also, this species can act as a standard signal source against which the return signals from many samples can be compared. The nonresonant CARS can be implemented by focusing the excitation radiation into a sample of liquid that produces a CARS/CSRS signal in the same frequency band as that generated from the sample. For example, benzene will generate a CARS anti-Stokes signal in the 3000-3100 $cm^{-1}$ frequency band.

Continuum generation is another type of nonresonant nonlinear process that can be used in the reference generator. A sufficiently high peak power pulse is focused into a medium, where it excites a broad bandwidth of frequencies to be produced. If the produced frequencies overlap the emission frequency band produced in the sample, this portion of the continuum can act as a reference signal. The generated continuum must be created by a mechanism that is sufficiently stable to not be overly sensitive to fluctuations in oscillator intensity. An unstable reference signal will result in noise in the cross-correlation signal. The benefit of continuum generation is that is likely to create a broad bandwidth that will have signal in the emission bandwidth of the sample, so that the continuum need only be filtered for the needed frequency band. Also, if the oscillator employs continuum generation, it may already generate light within the emission bandwidth that can be used as a reference generator, eliminating a separate nonlinear process in the reference generator step. Some examples of materials used for continuum generation materials are optical glass, fused silica, calcium fluoride, sapphire, ethylene glycol, water, high numerical aperture optical fibers, photonic crystal optical fibers, microstructured optical fibers, dispersion-shifted optical fibers, and gas cells (e.g. cells filled with helium, argon, or nitrogen).

Other candidate processes for nonresonant nonlinear reference generation include second and higher harmonic generation, stimulated Raman scattering, sum and difference frequency generation, optical parametric amplification, four-wave mixing, and self phase modulation.

Figure 5:
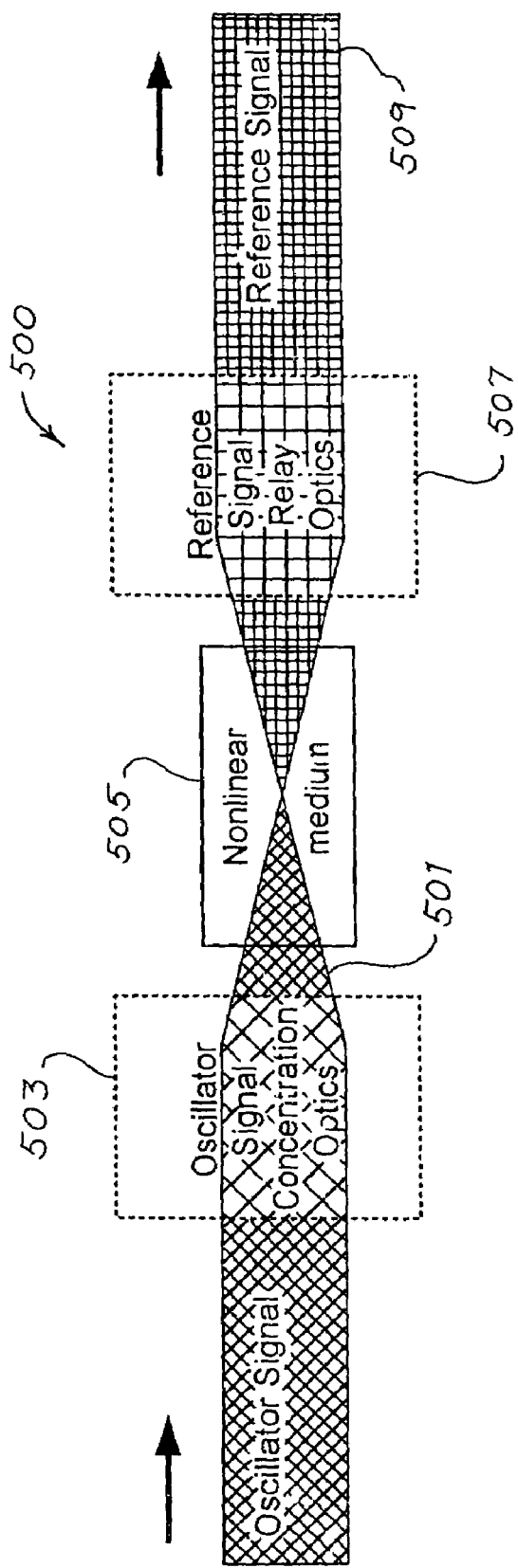
FIG. 5. Reference Signal Generator Implementation

FIG. 5 shows an implementation of a reference signal generator 500. The concentration optics 503 are typically implemented as some combination of lenses and mirrors. The concentration optics may also require some combination of frequency dispersive elements such as prisms, diffraction gratings, pulse shapers, and dispersive materials to prepare the temporal shape of the signal for nonlinear generation. Concentration in space and time may be necessary because the nonlinear processes are power sensitive, and depends on the strength of the nonlinear process. When the light 501 enters the nonlinear medium 505, it undergoes conversion to a frequency band coinciding with the frequency band of the response signal from the sample. This nonlinear medium may be one of the media mentioned above, either a sample of a target molecule, a solvent, or a continuum generation medium. After exiting the nonlinear medium, the reference signal 509 is collected by reference collection relay optics 507, where it is sent to the demodulator where it is combined with the sample signal. The collection relay optics are usually implemented as some combination of lenses and mirrors that collimate the reference field radiation. This reference field should be characterized to find its temporal structure by instruments such as Frequency Resolved Optical Gating, cross-correlation with another known signal, nonlinear sonograms, or nonlinear autocorrelations/cross-correlations.

3. Microscope.

The microscope delivers the excitation radiation from the oscillator to the sample and collects the resulting sample emission. Inside the sample, a coherent nonlinear process such as CARS or CSRS takes place that, in the presence of a molecule of interest, will emit the sample field in response to the excitation field. The sample field is collected by the microscope and then propagated to the demodulator, where the sample field can be estimated from the measured cross-correlation between the sample field and reference field.

Microscope systems can be differentiated by various implementation choices. They can either illuminate one (serial scanning) or many points (full field imaging) at a time on the tissue. If the pump and Stokes (anti-Stokes) beams of the excitation field are separated in frequency, they can be sent in either separate (non-collinear) or identical (collinear) angles into the sample. The temporal delay of the response radiation relative to the reference may or may not be used to range molecular constituents in the tissue. The response radiation can be collected in the forward scattering (forward CARS/CSRS) or backward scattering (epi-CARS/CSRS) directions.

The microscope measures spatially resolved molecular density by illuminating various points on the tissue with the oscillator field, collecting the emitted sample field, and recombining with the reference field in the demodulator. One point in the tissue may be illuminated at a given time, resulting in serial or raster scanning of the molecular density through the tissue. Alternatively, a line or a complete plane of points may be illuminated, so that data may be acquired from many points in parallel. Illuminating and measuring the radiation from an entire plane of points is called full field imaging. At the time of this writing, full field imaging is seldom used because it requires an array intensity detector such as a charge-coupled-device (CCD) to simultaneously measure the demodulated signals of all of the illuminated points. Unfortunately, as of this writing CCD arrays produce thermal dark noise at each pixel, and also have a relatively limited dynamic range of measurable intensity values. Demodulated interference signals often require very high dynamic range detection. It is conceivable that future CCD or other types of focal plane arrays (e.g. CMOS arrays) may overcome these limitations. Full field imaging also requires that the tissue be illuminated by larger amounts of power because measurable signal must be produced for an entire area rather than just one point. Since this is more likely to result in tissue damage, full field imaging will probably be used when speed of acquisition is paramount.

Figure 6:
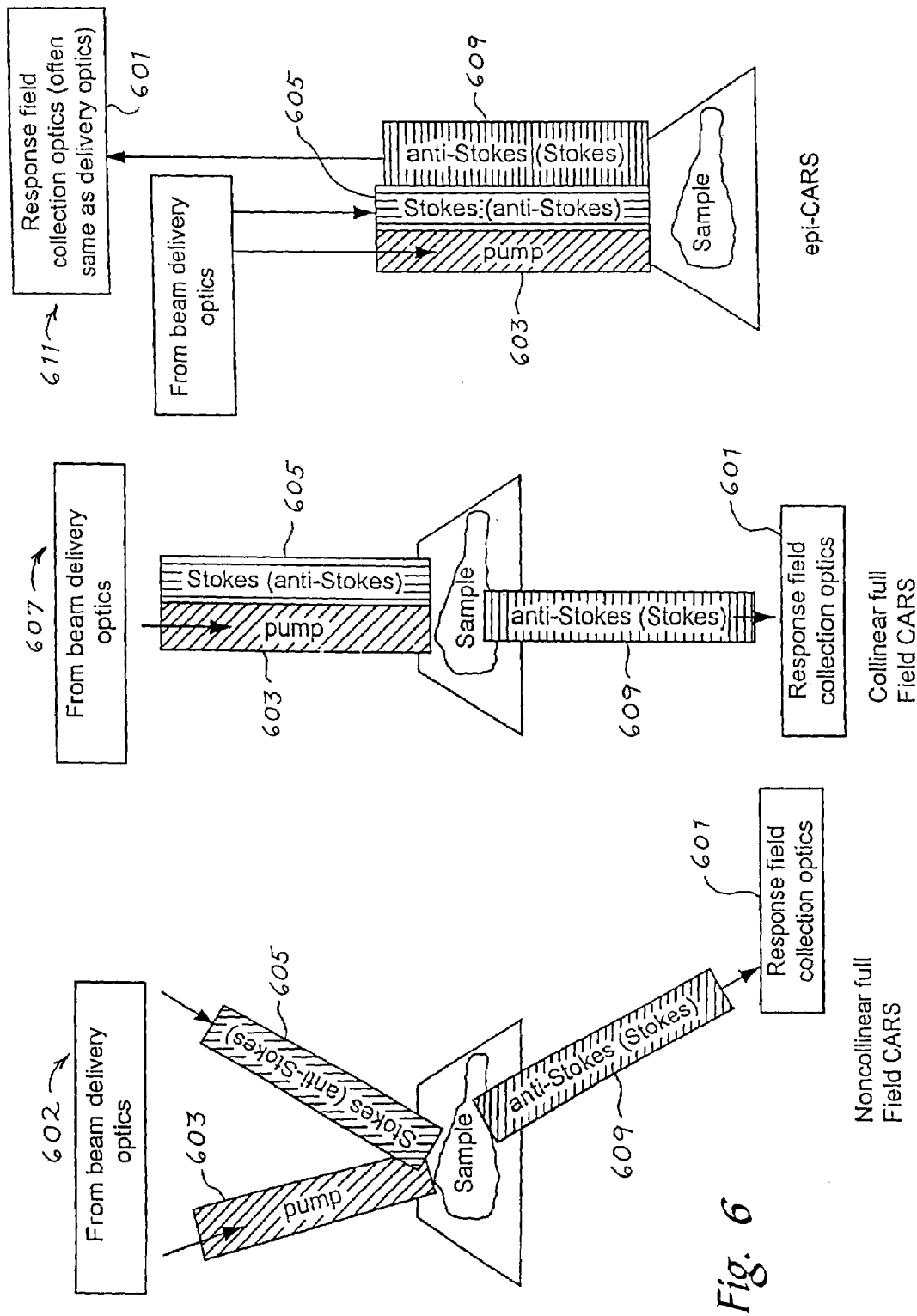
FIG. 6. Configurations for full field CARS.

FIG. 6 shows three examples of full field CARS configurations. The "beam delivery optics" are usually implemented as some combination of mirrors and lenses that deliver beams that illuminate a wide area or line on the sample. For all of these microscope configurations, beam delivery and collection optics will typically utilize a microscope objective. The "response field collection optics" 601 are similarly implemented as a combination of lenses and mirrors that relay the response field to the demodulator so that it may be recombined with the reference and detected. The noncollinear full field CARS 602 delivers the pump 603 and the Stokes 605 beams (assuming they are separate) at separate angles, so that the response is separated in angle from the illumination by an angle given by phase-matching conditions. The collinear geometry 607 sends the pump and Stokes radiation in the same directions (or in a single field if they can not be separated) and collects the radiation in the same direction, which can be discriminated with a dichroic beamsplitter. The epi-CARS geometry 611 collects the backscattered radiation, usually through the same objective optics that the sample is illuminated through. The epi-CARS can be discriminated from the illumination with a dichroic beamsplitter or an interference filter.

If collinear CARS is used, where the pump and Stokes (anti-Stokes) beams from the excitation beams overlap, then the response field 609 will overlap the excitation beams. Then the response field frequency band should not completely overlap the excitation frequency band, so that a spectral filter may distinguish between the excitation and response fields. If non-collinear CARS is used, then the response beam can be sufficiently angularly separated (as determined by the phase-matching criterion) from the excitation radiation to be filtered by a spatial filter. However, in the case of non-phase-matched CARS, such as epi-CARS, the interaction CARS volume must be small enough so that the response is radiated effectively isotropically, so that spatial filtering is unavailable and spectral filtering should be used.

The other, more commonly used alternative is serial point scanning. Serial scanning tightly focuses the oscillation signal into the tissue to create a very small volume where peak power is maximized. The focusing is usually achieved using a microscope objective. This focus is then scanned through a 3-D set of points in the tissue, and the sample signal gathered from each point is demodulated to produce a 3-D NIVI image. Since nonlinear processes are power sensitive, efficient CARS/CSRS occurs only at the focus. If the sample is small enough, the focus may be scanned through the sample by translating the sample in all three dimensions. However, it is not feasible to move large samples such as human subjects this way. In this case, the beam focus can be moved in the transverse direction by steering the beam, perhaps using galvanometer rotated mirrors, acousto-optic modulators, or translating the lens assembly. The depth may be scanned by mechanically adjusting the distance between the lens and the tissue, perhaps using a lead-screw translator and/or a piezoelectric transducer. Since the signal can be excited at only one point at a time, one can be sure that the resulting measured sample signal is due to the interference of emissions of radiation produced in that volume only. This can be a benefit in NIVI when high phase resolution is required because one is assured that any measured phase shifts are not due to interference between molecules at disparate spatial locations. This higher phase resolution may be used to better differentiate between similar molecular species. Serial point scanning typically utilizes a single photodetector or a small number of photodetectors at the demodulator, which has the benefit that the dark current of a single photodetector is usually less than that of an entire CCD array, and a single photodetector can also typically handle a higher dynamic range of measurements.

Figure 7:
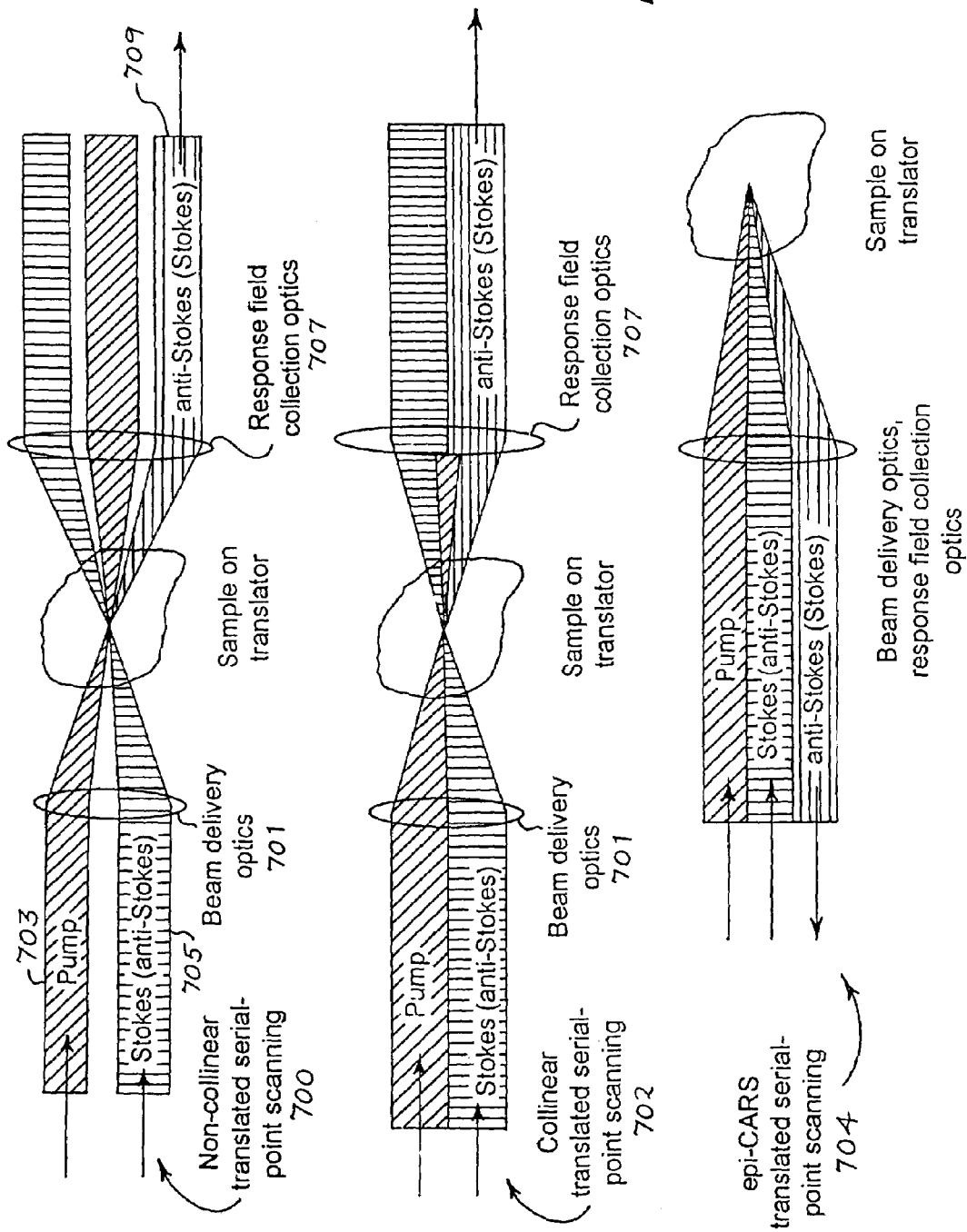
FIG. 7. Translated serial-point scanning configurations

FIG. 7 shows the geometry of translated serial-port scanning configurations. In all of these configurations, the sample is on a translator that moves the sample through the focus to form an image of the molecular density at various points. The translator could be a three-axis linear screw drive translator, or piezoelectric translator, or a combination of these. The beam delivery optics 701 focuses the pump 703 and Stokes (anti-Stokes) 705 beams onto the tissue at a point of interest, and the response field collection optics 707 gathers the generated anti-Stokes (Stokes) field 709 from the tissue. In the non-collinear geometry 700, the pump and Stokes illuminate the point of interest at different angles, so that the anti-Stokes will emerge at a third angle given by phase-matching, so that the anti-Stokes is spatially separated from the illumination. In the collinear geometry 702, the illumination and response fields emerge overlapped, so that they must be discriminated by frequency (e.g. using a dichroic beamsplitter). Finally, in the epi-CARS geometry 704, the backscattering response fields are collected, often by the same optics through which the illumination is projected, and can be separated with a dichroic beamsplitter.

Figure 8:
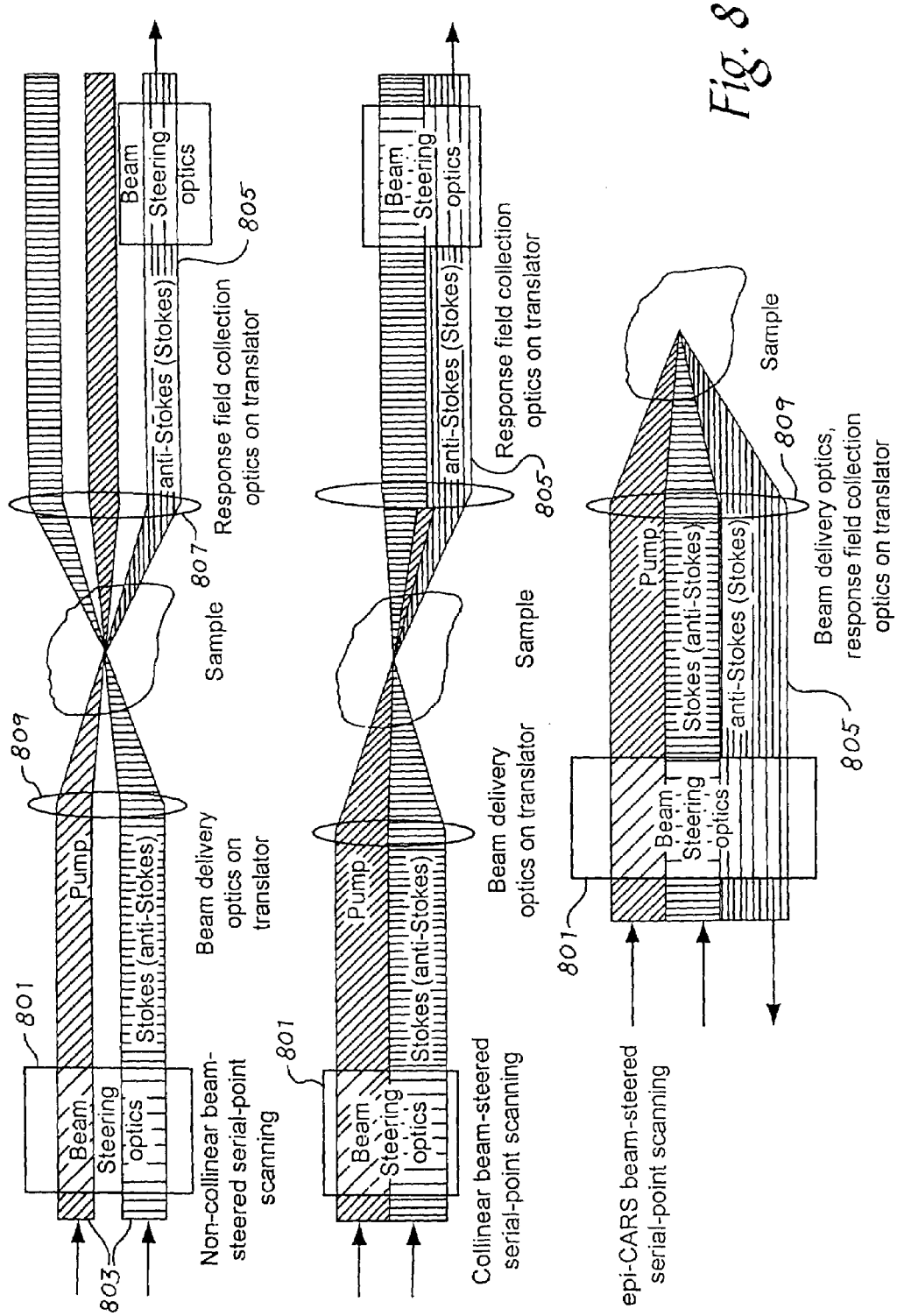
FIG. 8. Beam-steered serial-port scanning configurations

Alternatively, the focus can be moved and the sample can be left stationary. This can be accomplished by a combination of tilting the illumination beams before it enters the beam delivery optics and/or translating the beam delivery optics around (FIG. 8). Translating the collection optics and/or tilting the exiting response beam with a beam steering optics 801 can capture the exiting response field. The beam steering optics changes the direction of the incoming beam 803. This can be implemented, for example, by a galvanometer-scanned rotating mirror. By changing the direction of the beam before it enters the beam delivery optics 809, the position of the focus in the sample can be changed. The translation for the beam delivery and collection optics 807 can be implemented with a piezoelectric and/or a linear screw-drive translation stage. Translating the beam delivery and/or collection optics moves the focus with the optics through the sample. These two mechanisms can be combined to enable the three-dimensional translation of the focus through the sample. This configuration is especially convenient for the epi-CARS configuration, because the same beam steering optics and beam delivery optics 809 can be used to collect the response field 805. For these configurations, a compensating delay may need to be incorporated into the demodulator because steering the beam and/or translating the delivery and collection optics change the travel time for the illumination and response signal through the microscope section.

All of the previous scanning modes, full field imaging, translated serial-point scanning, and beam-steering serial-port scanning, use the spatial location of the illumination beam to differentiate between response signal gathered from various points in the sample. This confinement method is the same as that used by multiphoton microscopy or CARS microscopy. Other technologies such as Optical Coherence Tomography and Optical Coherence Microscopy use temporal ranging in addition to spatial confinement to further isolate the contributions of signal from various points in the sample. Because of the heterodyne nature of NIVI, this scanning mode is also available. It may be attractive for in vivo imaging because it will enable scanning tissue without translating the microscope objective or sample, and may scan faster because there are mechanisms for scanning the temporal delay much faster than translating objective optics. The phase measurement capability of NIVI is useful for both temporal ranging and molecular species identification this way.

Figure 9:
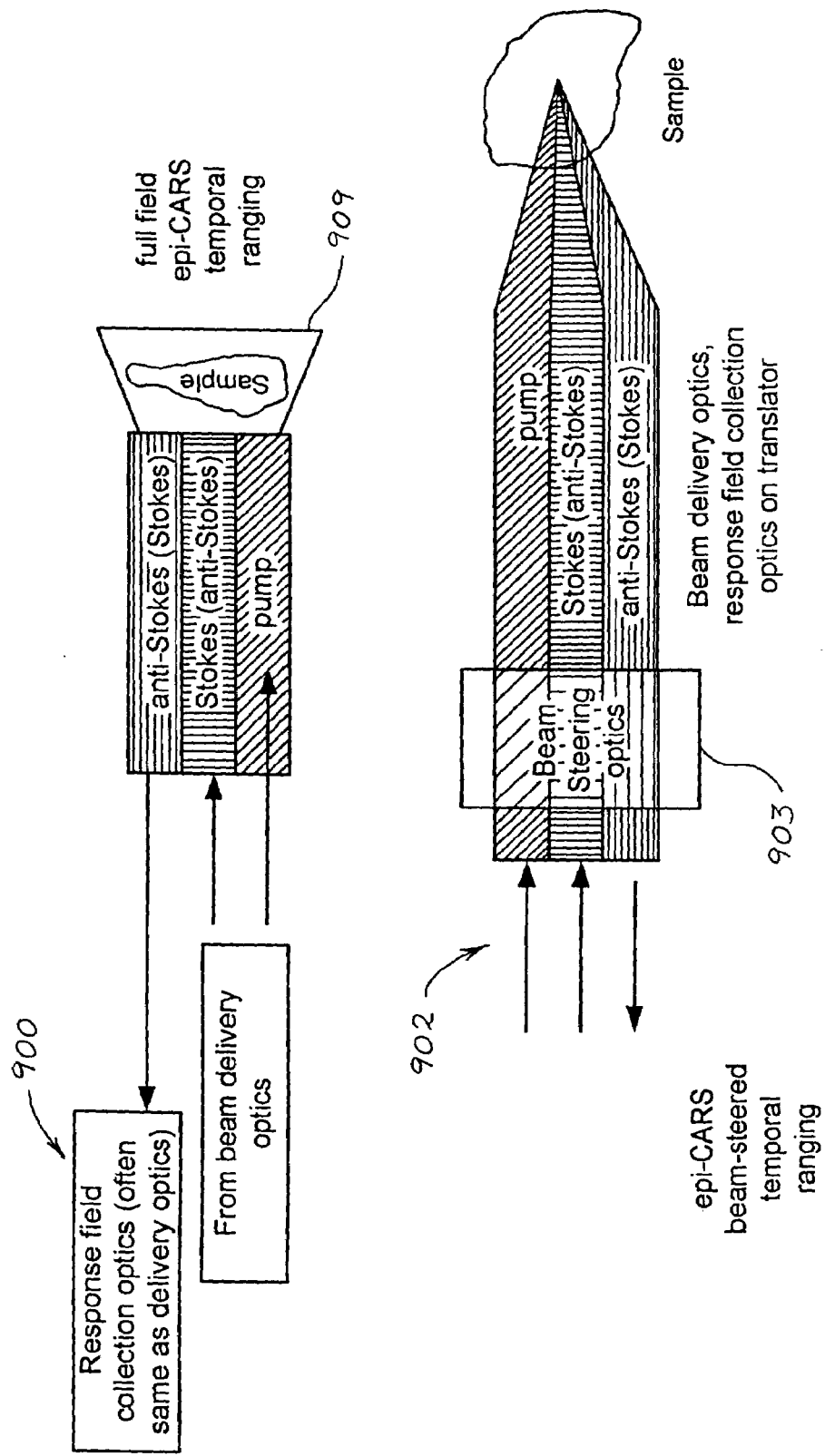
FIG. 9. Temporal-ranging based NIVI

FIG. 9 shows two configurations of NIVI 900 and 902 utilizing temporal ranging. Temporal ranging is achieved by measuring the interference of the reference and response signals for various relative temporal delays. The temporal gating configuration superficially resembles the other epi-CARS configurations. However, unlike previous scanning modes, the depth-of-field of the focusing of the illumination from the beam delivery optics in the tissue is set to be long, because the temporal gating will be used to discriminate between molecular constituents within the depth-of-field. This temporal ranging utilizes epi-CARS/epi-CSRS because the backscattered response signal is collected from the sample by the response field connector so that the signal delay into the tissue can be timed. Because CARS/CSRS is not phase-matched for the backwards direction, the generation of a backscattered signal will only occur efficiently for small particles or edges of particles with a compatible resonance. The chief difference between this configuration and the other epi-CARS configurations is that the interference signal is scanned as a function of relative delay, and an interference signal maximum indicates the presence of a molecular species at a particular depth in the medium (corresponding to that time delay). In the full field configuration 900, an entire plane of points is interfered with the reference signal to produce simultaneous measurements of the cross-correlation signal for the entire plane 909. By scanning the delay, the molecular density of various planes can be measured. For the beam-steered temporal gating setup 902, the beam is scanned through the sample by tilting the beam through the beam steering optics 903. Beam steering provides lateral displacement of the beam, and temporal gating provides depth information so that a three-dimensional volume is scanned. The sample can be translated laterally also to scan the beam. The implementation differences between the temporal gating configurations are in the choice of depth-of-field of the illumination and collection optics, and in the demodulator. The demodulator must be designed to scan a sufficient temporal interval to capture the interference signal between the reference and response signals. This temporal interval is typically between 500 microns to 10 mm.

4. Demodulator.

The purpose of the demodulator section is to decode the response signal from the sample so that it may be measured by relatively slow electronic equipment (slow compared to the oscillations of the electric field of the response signal). The magnitude of this demodulation signal will be related to the density of a molecular species of interest in the tissue. With knowledge of the molecular density at each point, a molecular density map, or NIVI image, can be presented to the user. This demodulation is implemented as the cross-correlation of the response signal relative to a generated reference signal. Outlined below are various optical configurations that produce this cross-correlation signal.

There are various design choices that are made when choosing a demodulator. First, one needs to know whether or not full field microscopy is used. Also, one must decide whether the cross-correlation will be measured one sample at a time, or many samples in a single instant.

Figure 10:
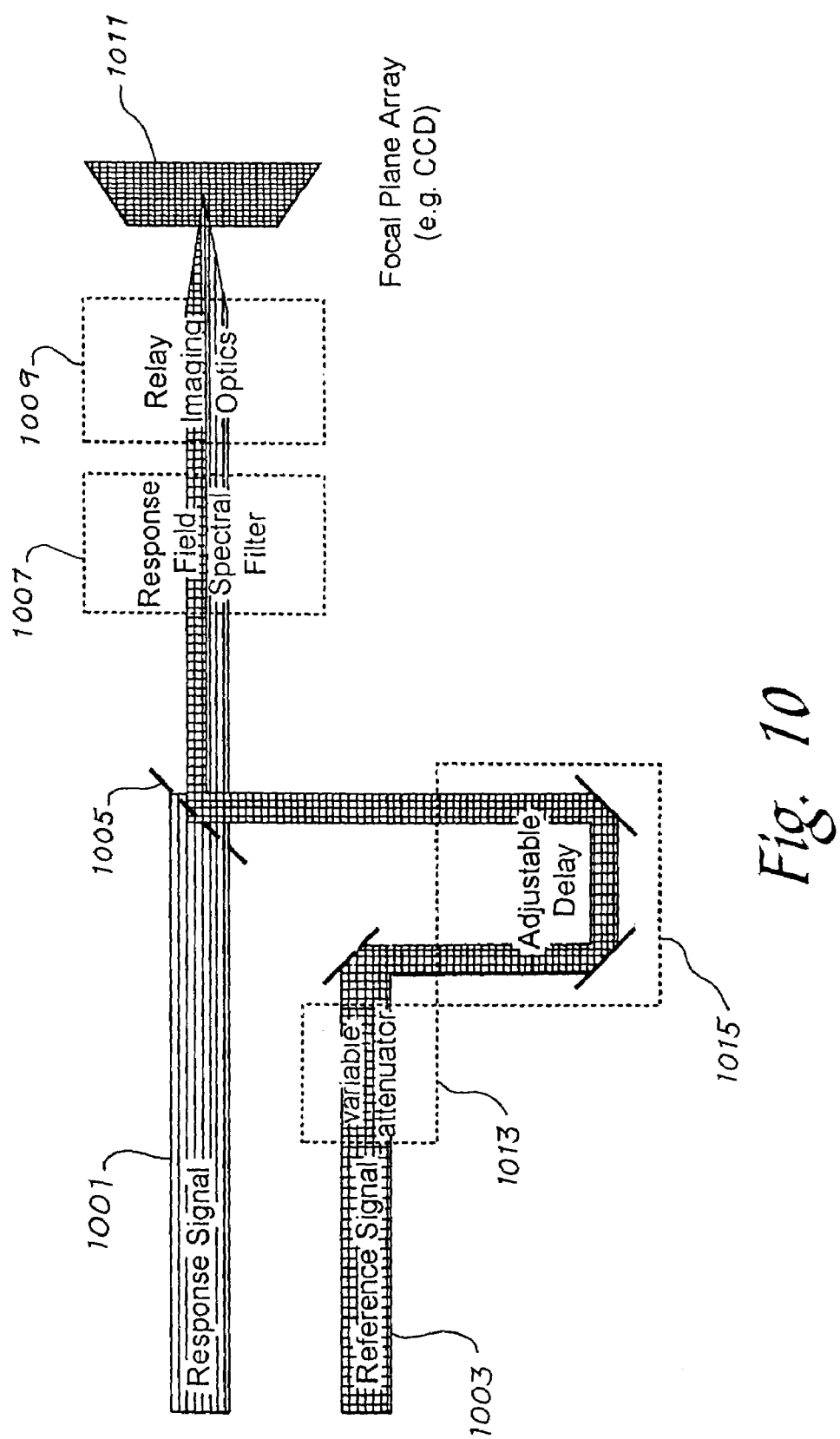
FIG. 10. Full field cross-correlator demodulator

FIG. 10 shows an example of a cross-correlator that can be used to demodulate the full field CARS signal, measured for example as in FIG. 6. The response field is collected and relayed by the "response field collection optics" of FIG. 6 to the Response Field 1001 of FIG. 10. The reference field 1003 is produced by the Reference Generator and relayed to the cross-correlator. The reference is delayed relative to the response field, and they are mutually overlapped using a beamsplitter 1005. The "response field spectral filter" 1007 filters the recombined field for only the frequency band that contains the response field bandwidth, which removes any remaining oscillator signal. The filter can be implemented by a combination of interference filters, color glass filters, dichroic beamsplitters, or other frequency selective elements. The combined fields are imaged onto a focal plane array 1011, such as a CCD, so that the CCD is the conjugate image plane of the sample plane. The imaging is achieved with the "relay imaging optics" 1009 which are some combination of lenses and mirrors. The intensity detected on the CCD corresponds to a single cross-correlation signal measurement collected from various points in the sample. The "variable attenuator" 1013 is adjusted to maximize the use of the dynamic range of intensity measurements of the CCD. As the focus in the sample changes (e.g. by translating the sample), and/or the adjustable delay 1015 is changed, the entire cross-correlation signal can be measured, forming a three-dimensional data set. The typical scan range length for high numerical aperture full field imaging will be up to 100 microns. The delay can be implemented as a mirror translated by a linear-screw-drive translation stage, or by piezoelectric actuation. This same cross-correlation can also be used for temporal ranging full field NIVI, as shown in FIG. 9, with the only difference being that the delay mechanism must be designed to scan a sufficiently long range of interest in the sample, typically from 500 microns to 10 mm.

The measurement of a cross-correlation signal for a serial-point scanning microscope is basically the same system as for full field imaging, except that a single photodetector can be used rather than an array photodetector. The adjustable delay, response field spectral filter, and relay imaging optics can all be implemented in similar ways to the full field case. The relay imaging optics will need only focus the combined response/reference signal onto the photodetector. In some cases, when only the magnitude of the cross-correlation signal at its peak needs to be measured, it may be desirable to dither the adjustable delay with a piezoelectric transducer a fraction of a wavelength, so that the magnitude of the cross-correlation signal peak can be demodulation with a multiplying mixer and low-pass filter (an electronic heterodyne demodulator). This configuration will be covered in more detail in part five. To measure the entire cross-correlation, the adjustable delay will be scanned over various time delays and the photodetector intensity signal measured.

Figure 11:
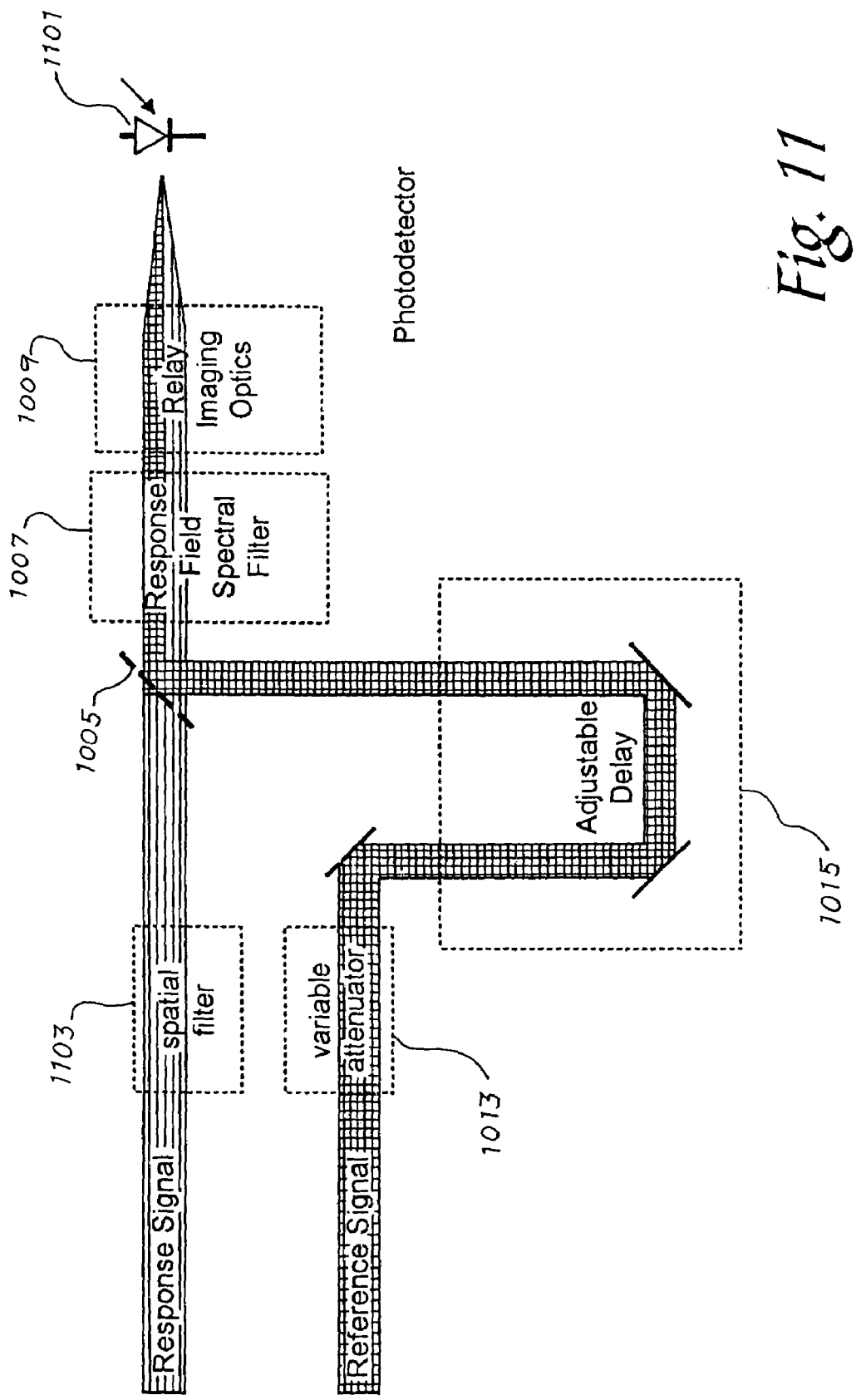
FIG. 11. Temporal cross-correlator for a serial-point scanning microscope.

In FIGS. 10 and 11, a variable attenuator 1013 is used to adjust the intensity of the signal that reaches the photodetector 1101 so that its dynamic range is not exceeded. Variable attenuators can be implemented with liquid crystal shutters, neutral density filter wheels, or rotating polarizers. The spatial filter 1103 is used on the response signal to filter out spatial inhomogeneities in the response signal that could reduce the depth of modulation at the photodetector. A spatial filter would typically consist of a telescope of two converging lenses, with a pinhole in the focal plane between the lenses to filter out power around the main diffraction focus.

Figure 12:
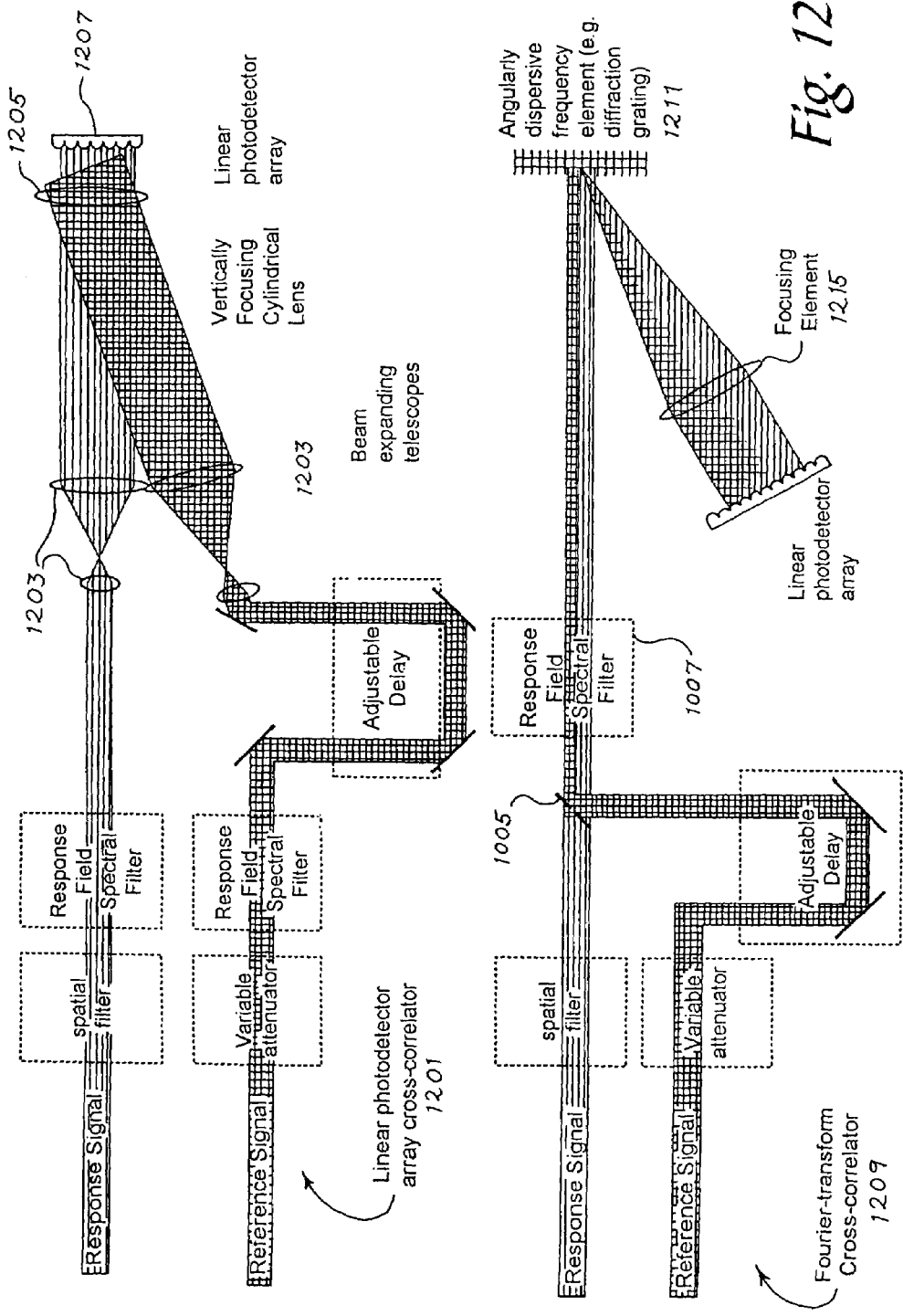
FIG. 12. Shown are two configurations that utilize linear photodetector arrays to measure multiple samples of the cross-correlation simultaneously.

When the oscillator produces pulses of a low repetition rate, so that for example high peak power can be employed, one may want to measure multiple samples of the cross-correlation signal simultaneously. This can be achieved by the configurations in FIG. 12. These configurations have the advantage that, with a sufficient amount of pulse power and number of photodetector array samples, the cross-correlation signal can be measured using a single pulse. Low repetition rate illumination can keep the peak power high while average power remains low.

The "linear photodetector array cross-correlator" 1201 expands the response and reference signals, and interferes them with an angle between the two beams. The beam expansion is achieved by, for example, a pair of converging achromatic lenses 1203 arranged in a telescope configuration. The points on the wavefront where the two signals combine will have various time delays between them. A cylindrical lens 1205 then focuses the beams into a line image on a linear photodiode array 1207. This concentrates the signal to adjust for the narrow height of the detector pixels. Each intensity sample on the linear photodetector array indicates a sample of cross-correlation of the two fields with various relative time delays, with a constant intensity signal added. The recorder would then read the linear CCD signal so that a complete NIVI image can be assembled.

The primary disadvantage of this system is that the modulation of the intensity signal on the linear photodetector array is rather low, and the dynamic range of typical CCDs is likewise low, so that the signal cannot be measured to a high signal-to-noise ratio. To combat this, one can utilize the Fourier-transform cross-correlator 1209. Rather than directly measuring samples of the cross-correlation, it interferes the two signals and measures their spectral decomposition. The beamsplitter 1005 combines the response and reference signals, which are filtered for the response bandwidth by utilizing a response field spectral filter 1007. This signal is then filtered by a frequency dispersive element 1211 such as a diffraction grating that scatters each frequency to a different angle. The power of each frequency is then focused to a different pixel on the linear photodetector array 1215 by using a focusing element 1213 (typically a combination of lenses or mirrors). The samples of the intensity measured on the photodetector indicate the real part of the Fourier transform of the cross-correlation signal. The recorder may compute an inverse discrete Fourier transform of the linear photodetector array intensity samples to recover the cross-correlation. The Fourier transform already performs the necessary Hilbert transform to infer the imaginary part of the cross-correlation signal. However, because it is an intensity measurement, the cross-correlation signal, a time-reversed version, and the autocorrelation of the response signal are superimposed in the intensity signal. By choosing the adjustable delay longer than the length of the cross-correlation temporal signal, the reconstruction of these signal components will not overlap in the time domain, and so the recorder device may distinguish the cross-correlation from its mirror image and the autocorrelation.

The adjustable delay may also be dithered a small amount to introduce a phase shift into each measured frequency component at the linear photodetector array. By utilizing at least three linearly independent phase shifts, the phase of each Fourier component can be known and the time domain cross-correlation computed using an inverse discrete Fourier transform. However, then the ability to measure the cross-correlation of a single pulse will be lost. Another possibility is to use a linear photodetector array with several rows (at least three) rather than just one row of pixels. By tilting one of the wavefronts slightly vertically with respect to the other, a small phase shift can be introduced in the measured cross-correlation signal between rows on the linear photodetector. With a sufficiently large phase shift, the complex amplitude of each Fourier component can be inferred from the intensity samples from each column on the linear photodetector by utilizing the discrete Fourier transform. Since all of the time delayed cross-correlation samples are measured simultaneously, this is a single-pulse measurement.

To minimize the effect of dark charge built up in the linear CCD detector, it is best to discard the charge as soon as possible before the pulse arrives, and read the CCD as soon as possible after the pulse arrives. The speed of readout should be as fast as possible given limitations in accuracy due to the readout noise.

5. Record r.

The recorder accumulates the samples of the cross-correlation signal gathered from various points in the sample, processes this data, and presents these as a human-interpretable image. It is usually implemented as a data acquisition digital computer with some method of automatic control of the adjustable mechanisms (such as delay lines, piezoelectric actuators, and galvanometer mirrors), analog-to-digital conversion, and some form of image output device such as a screen or printer. It may also have control of the oscillator itself, to automatically tune the wavelengths or bandwidths of output or control the rate or timing of pulse output. It may also control the delay lines or spatial light modulators in the pulse shaping mechanisms of FIG. 4.

Typically, the recorder will scan the illumination through the sample and/or the adjustable time delay and measure the cross-correlation signal. Unless the Fourier-Transform cross-correlator is used, the intensity samples represent the cross-correlation signal with a constant level added that could be discarded. The magnitude of the cross-correlation signal indicates the presence of the target molecular species. For CARS/CSRS the magnitude of the cross-correlation signal is related to the second power of the molecular density of that species. By demodulating the magnitude of the cross-correlation signal, the molecular density can be estimated for the points on the cross-correlation signal for the areas from which the response signal was collected to form that cross-correlation signal. Both spatial confinement and temporal ranging can be used to differentiate between the signals due to molecular densities at different locations in the sample.

Figure 13:
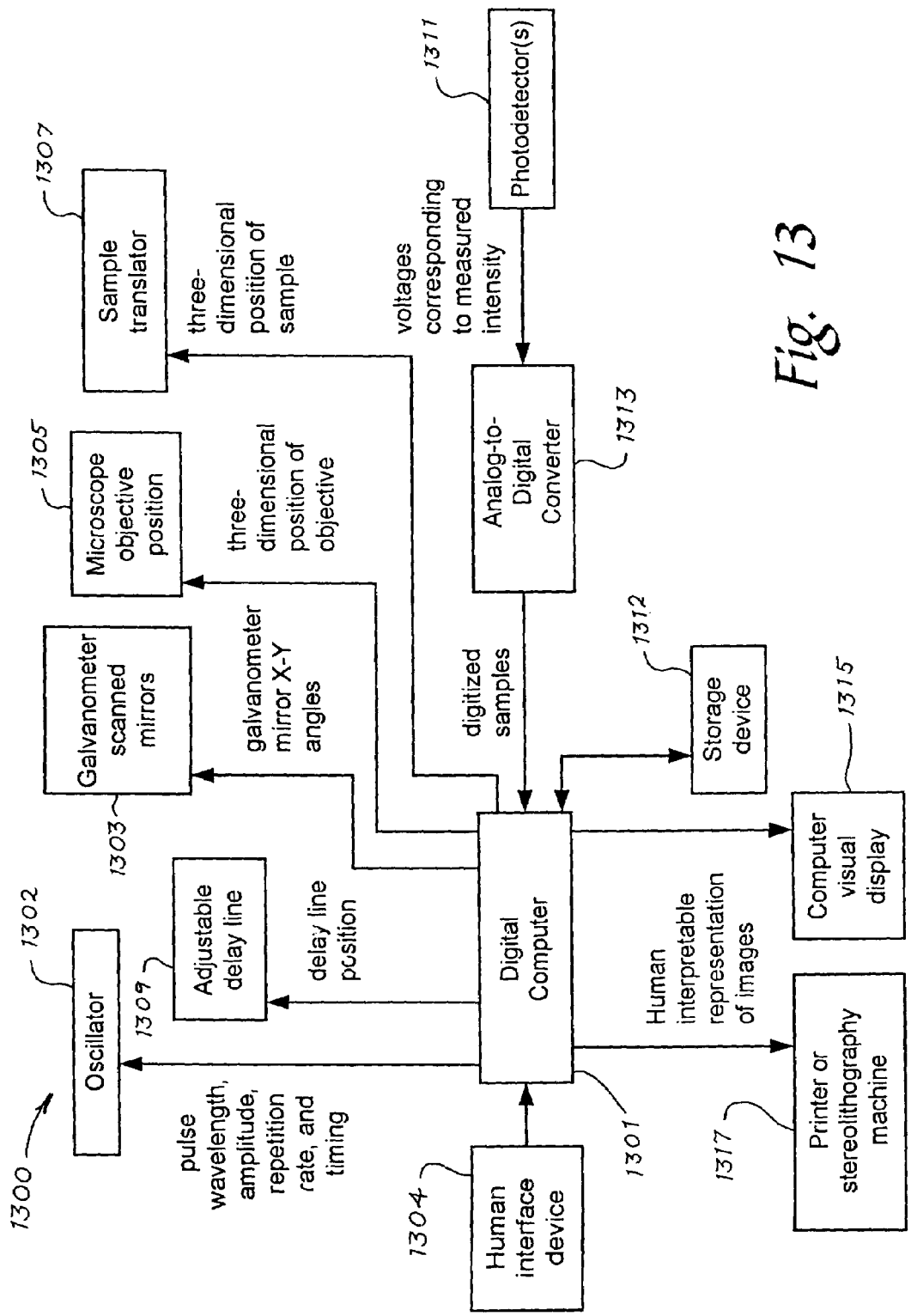
FIG. 13. Diagram of an implementation of the recorder.

FIG. 13 documents the relationship between the elements of the recorder 1300. For serial-scanning or temporal-scanning configurations, the instructions from the operator are entered via a human interface device 1304 into the digital computer 1301. The digital computer controls the scanned beam position in the sample using the galvanometer mirror angles of the galvanometer scanned mirrors 1303, the oscillator 1302, the adjustable delay line 1309, the position of the microscope objective position 1305, and/or the position of the sample translator 1307 to scan the illumination through the sample. In general only a subset of these need be controlled to scan the three-dimensional volume of the tissue. If full field imaging is used, usually only the depth and/or the delay line need be scanned. The cross-correlation signal as measured by the intensity is converted to a voltage by the photodetector 1311, which is in turn converted to a digital sample by the analog-to-digital converter 1313. The digital computer varies the delay line and/or reads various pixels from the photodetector (if it is an array detector) to determine the cross-correlation signal. If a Fourier-transform cross-correlator is used, the computer will need to compute the inverse discrete Fourier transform of the signal to find its cross-correlation from the intensity samples. The computer then associates the magnitude of the cross-correlation signal with the molecular density, and assembles these magnitudes into a density map of the sample. This density map is stored in the storage device 1312 presented on the visual display 1315 and/or made into a physical representation with a printer or stereolithography device 1317.

Figure 14:
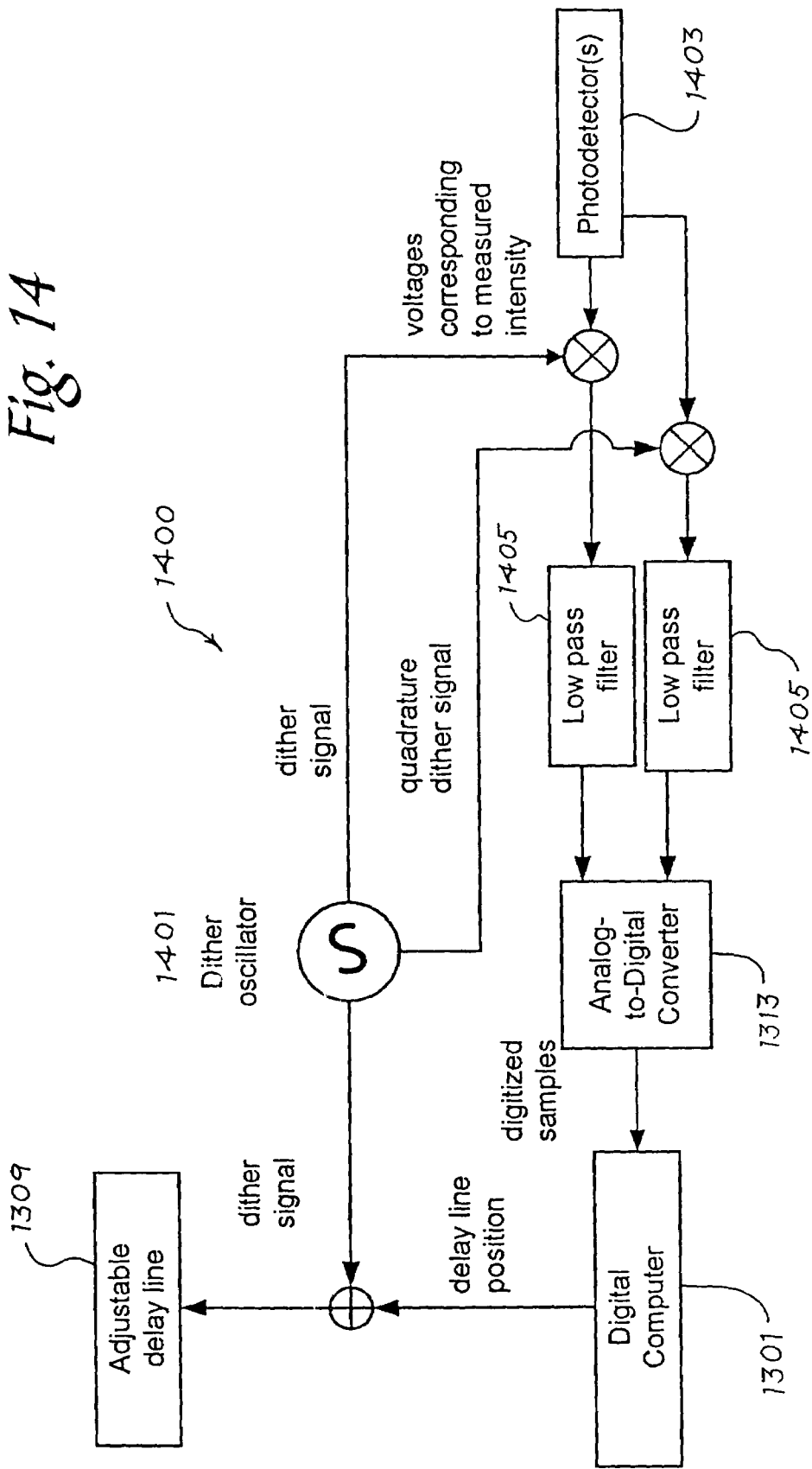
FIG. 14. Electrical cross-correlation signal quadrature amplitude demodulator.
Figure 15:
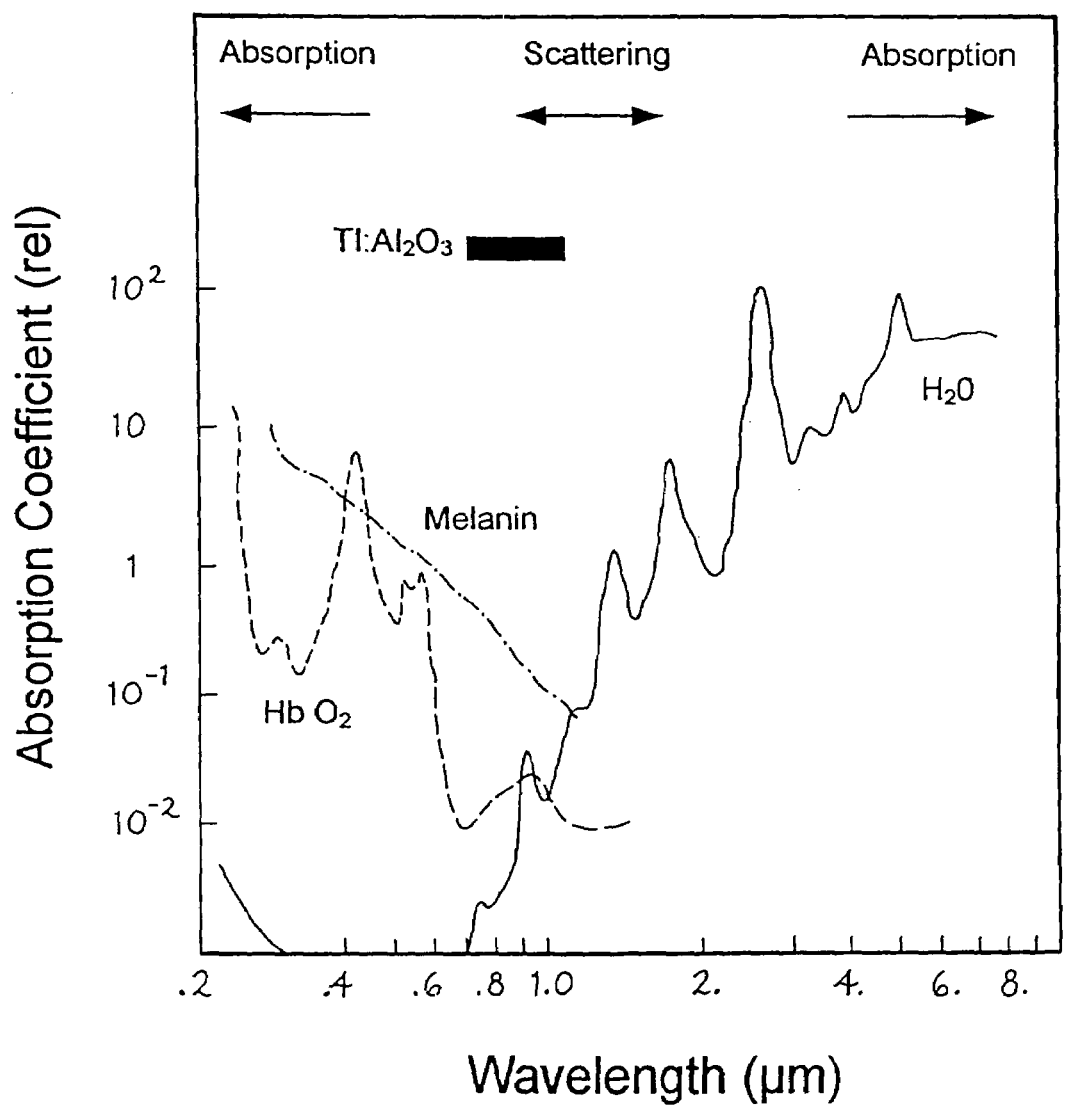
FIG. 15. "Biological window" in tissue where absorption of near-infrared wavelengths is at a minimum and light can penetrate deep into highly-scattering tissue.

To aid in the measurement of the magnitude of the cross-correlation signal, the configuration 1400 of FIG. 14 is suggested.

Because the digital computer 1301 can record only relatively slow signals, a dither oscillator 1401 may be used to add a small high-frequency dither signal into the adjustable delay line 1309 that produces a periodic perturbation of the delay in the signal of a magnitude usually of less than one wavelength. This same signal is multiplied by the received photodetector 1403 interference signal to demodulate it, and is low pass filtered through the low pass filters 1405 to remove harmonics of the dither frequency. Both the dither and its quadrature signal are demodulated, because these correspond to the real and imaginary parts of the complex cross-correlation amplitude. The analog-to-digital converter 1313 will then be directly measuring a quantity proportional to the complex magnitude of the cross-correlation for the delay line position. The computer can utilize the digitized real and imaginary cross-correlation components to display the amplitude and phase of the cross-correlation signal. The amplitude will correspond to the magnitude of the reflection, and the phase will correspond to the Doppler shift of the reflection. If a very fast dither signal is desired (above 10 kHz), an electro-optic modulator or acoustical-optic modulator can be placed in the adjustable delay line system to rapidly modulate the delay a small amount.

The magnitude of the cross-correlation signal depends both on the density of molecules available to produce the response signal, and on the temporal structure of the signals radiated from the molecules. The temporal signal produced by the molecules can be inferred from the cross-correlation signal. If f(t) is the temporal response signal produced by a molecule, and g(t) is the known reference signal, the measured cross-correlation $\Gamma(\tau)$ is given by:

$$\Gamma(\tau) = \int_{-\infty}^{\infty} f(t)g(t-\tau)dt$$

If $\tilde{F}(\omega)$, $\tilde{G}(\omega)$, and $\tilde{\Gamma}(\omega)$ are the Fourier transforms of f(t), g(t), and $\Gamma(\tau)$ respectively, then $\tilde{\Gamma}(\omega)=\tilde{F}(\omega)\tilde{G}(-\omega)$. The function $\tilde{\Gamma}(\omega)$ can be computed from the Fourier transform of the cross-correlation and $\tilde{G}(\omega)$ can be computed from the measured reference signal. The Fourier transform $\tilde{F}(\omega)$ of temporal signal f(t) can then be estimated by $\tilde{F}(\omega)=\tilde{\Gamma}(\omega)\tilde{G}(-\omega)\cdot/(\tilde{G}(-\omega)^2+N(\omega)^2)$ (change to equation), where $N(\omega)$ is an estimated power-spectral-density of the noise. An inverse Fourier transform of $\tilde{F}(\omega)$ yields f(t).

The recorder can perform this computation and thus recover f(t) for various molecular species. An unknown molecule may be identified by comparing its temporal signal to known molecular signals. In addition, by looking at the frequencies $\omega$ of phase arg $\tilde{F}(\omega)$ where the phase changed rapidly, the resonance frequencies of the molecules of interest can be determined to high precision. A library of the temporal responses and resonance frequencies of various molecules for CARS excitation may be built up and used to identify unknown molecules in vivo. We also note that the same cross-correlation measurement configurations can be used to measure the OCT backscattered signal due to the scattering of the excitation radiation. To do this, the excitation and response bands should be separated with a dichroic beamsplitter, and the cross-correlation setups implemented separately to eliminate photon noise from the excitation band being measured in the response band. Different cross-correlation setups may be used for each configuration, e.g. a single-pulse measurement system for the conventional excitation and a time delay cross-correlator as in FIG. 11.

Embodiment

Randomness introduced into the measurement process may produce false positive indications of molecular densities, or obscure weak concentrations of molecular densities. This randomness has three sources: fluctuations in the oscillator, vibrations and air currents, and noise introduced by the photodetector.

Oscillator fluctuations are the hardest to characterize because the feedback mechanism of laser sources can produce large variations in the frequency, bandwidth, and output power of the pulses even for small perturbations of the oscillator. In addition, nonlinear processes such as self-phase-modulation, self-focusing (Kerr lensing), or continuum generation may also affect the pulse in ways that are sensitive to the power in the pulse. Therefore, it is desirable to keep fluctuations in pulse energy below a few percent, and keep frequency and bandwidth fluctuations under one percent.

Well designed state-of-the-art Ti-sapphire oscillators and regenerative amplifiers can meet these specifications if they are aligned and maintained within the guidelines set up by the manufacturer. It is important that the internals of the apparatus be shielded, as well as the paths of the beams, as much as possible from air currents and vibrations. This can be achieved by placing the apparatus on a platform with air flotation or shock-mounted legs. The oscillator apparatus should be enclosed in a rigid case with baffles that minimize the opening surface area to that required for the beams to enter and leave the case. It is best to use laser-diode or laser-diode-pumped solid-state sources to pump the oscillator to minimize pump fluctuations, but a well controlled ion laser is also usable.

A dispersion compensated mirror Ti-sapphire system can produce 200 nm or more bandwidth centered at 800 nm and is also suitable for the chirped-CARS or CARS utilizing a pulse shaper.

Another possibility is to employ a femtosecond diode-pumped erbium or ytterbium fiber laser. Fiber-based continuum generation sources of nanojoule energy have been demonstrated, and this source may be relatively inexpensive and compact. A pulse selector ("pulse picker") utilizing a Pockels cell or a fiber-based electro-optic modulator or electro-absorption modulator may be used to lower the average power while keeping the peak power high. A fiber amplifier can be used to increase the energy of the pulses. A fiber-based amplifier may provide a more portable, stable source.

If continuum generation is used, a source employing self-phase-modulation is preferable because of the short interaction length of the nonlinearity. For example, a microjoule energy pulse will broaden when focused into a fused silica, sapphire, calcium fluoride, or quartz medium. Self-focusing can be used to increase the peak power and minimize the interaction length. Self-phase-modulation in an optical fiber may be sufficient if it occurs over a short length of fiber. The fiber should be single mode in the bandwidth utilized to minimize nonlinear coupling of multiple modes. Higher peak power allows a stronger nonlinearity to be used and therefore minimizes the interaction length.

Photodetector noise is the other source of noise. There are two sources of photodetector noise: photon noise and thermal noise. Thermal noise may be eliminated by using a cooled detector, or by minimizing the integration time. If a line camera is used, the charge on the array can be expelled before the pulse is received and the signal can be read out immediately after the pulse is received. Also, the reference power should be balanced with the power received from the sample so that the dynamic range of the detector is utilized. Photon noise is fundamental to photodetection processes. Its effect can be minimized in several ways: using more illumination power to produce a larger CARS signal. Also, using the Fourier-transform cross-correlator minimizes the photon noise effect by increasing the modulation when single pulse illumination is used.

Equipment Brand Names:
Coherent Laser (of Coherent, Inc.) 10W Verdi pumps the
Kapteyn-Murnane Laboratories, LLC, titanium:sapphire seed (pump) laser
Which pumps the
Coherent Regenerative Amplifier (RegA 9050)
And uses the
Coherent Stretcher/Compressor.
A portion of the amplified light is sent to a
Coherent Optical Parametric Amplifier (OPA9450)
Which produces the second optical beam.

While we refer to a microscope (Leica) for beam delivery and holding the sample, any standard optics could be used. We are currently using a computer controlled 3-axis stage (Newport Corp.) to translate our samples under the imaging beams.

REFERENCES

1. Huang D, Swanson E A, Lin C P, Schuman J S, Stinson W G, Chang W, Hee M R, Flotte T, Gregory K, Puliafito C A, Fujimoto J G. Optical Coherence Tomography. Science 254: 1178-1181, 1991.

2. Fujimoto J G, Brezinski M E, Tearney G J, Boppart S A, Bouma B E, Hee M R, Southern J F, Swanson E A. Biomedical imaging and optical biopsy using optical coherence tomography. Nature Medicine 1:970-972, 1995.

3. Brezinski M E, Tearney G J, Bouma B E, Izatt J A, Hee M R, Swanson E A, Southern J F, Fujimoto J G. Optical coherence tomography for optical biopsy: properties and demonstration of vascular pathology. Circulation 93:1206-1213, 1996.

4. Schmitt J M, Knuttel A, Bonner R F. Measurements of optical properties of biological tissues by low-coherence reflectometry. Appl. Opt. 32:6032-6042, 1993.

5. Sergeev A M, Gelikonov V M, Gelikonov G V, Feldchtein F I, Kuranov R V, Gladkova N D. In vivo endoscopic OCT imaging of precancer and cancer states of human mucosa. Opt. Express 1:432-440, 1997.

6. Tearney G J, Brezinski M E, Bouma B E, Boppart S A, Pitris C, Southern J F, Fujimoto J G. In vivo endoscopic optical biopsy with optical coherence tomography. Science. 276:2037-2039, 1997.

7. Boppart S A, Bouma B E, Pitris C, Tearney G J, Southern J F, Brezinski M E, Fujimoto J G. Intraoperative assessment of microsurgery with three-dimensional optical coherence tomography. Radiology. 208:81-86, 1998.

8. Hee M R, Izatt J A, Swanson E A, Huang D, Schuman J S, Lin C P, Puliafito C A, Fujimoto J G. Optical coherence tomography of the human retina. Arch. Ophthalmol. 113: 325-332, 1995.

9. Puliafito C A, Hee M R, Lin C P, Reichel E, Schuman J S, Duker JS, Izatt J A, Swanson E A, Fujimoto J G. Imaging of macular disease with optical coherence tomography (OCT). Ophthalmology 102:217-229, 1995.

10. Puliafito C A, Hee M R, Schuman J S, Fujimoto J G. *Optical Coherence Tomography of Ocular Diseases*. Slack, Inc, Thorofare, N.J., 1995.

11. Schmitt J M, Knuttel A, Yadlowsky M, Eckhaus A A. Optical coherence tomography of a dense tissue: statistics of attenuation and backscattering. Phys. Med. Biol. 39:1705-1720, 1994.

12. Schmitt J M, Yadlowsky M J, Bonner R F. Subsurface imaging of living skin with optical coherence microscopy. Dermatology 191:93-98, 1995.

13. Sergeev A M, Gelikonov V M, Gelikonov G V, Feldchtein F I, Kuranov R V, Gladkova N D, Shakhova N M, Snopova L B, Shakov A V, Kuznetzova I A, Denisenko A N, Pochinko W, Chumakov Y P, Streltzova O S. In vivo endoscopic OCT imaging of precancer and cancer states of human mucosa. Opt Express 1:432-440, 1997.

14. Profio A E, Doiron D R. Transport of light in tissue in photodynamic therapy of cancer. Photochem. Photobiol. 46:591-599, 1987.

15. Tearney G J, Brezinski M E, Boppart S A, Bouma B E, Weissman N, Southern J F, Swanson E A, Fujimoto J G. Catheter-based optical imaging of a human coronary artery. Circulation 94:3013, 1996.

16. Tearney G J, Brezinski M E, Southern J F, Bouma B E, Boppart S A, Fujimoto J G. Optical biopsy in human gastrointestinal tissue using optical coherence tomography. Amer. J. Gastroenterol. 92:1800-1804, 1997.

17. Tearney G J, Brezinski M E, Southern J F, Bouma B E, Boppart S A, Fujimoto J G. Optical biopsy in human urologic tissue using optical coherence tomography. J. Urol. 157:1915-1919, 1997.

18. Boppart S A, Brezinski M E, Pitris C, Fujimoto J G. Optical Coherence Tomography for Neurosurgical Imaging of Human Intracortical Melanoma. Neurosurgery 43:834-841, 1998.

19. Bouma B E, Tearney G J, Boppart S A, Hee M R, Brezinski M E, Fujimoto J G. High resolution optical coherence tomographic imaging using a modelocked Ti:Al$_2$O$_3$ laser. Opt. Lett. 20:1486-1488, 1995.

20. Drexler W, Morgner U, Kartner F X, Pitris C, Boppart S A, Li X, Ippen E P, Fujimoto J G. In vivo ultrahigh resolution optical coherence tomography. Opt. Lett. 24:1221-1223, 1999.

21. Tearney G J, Bouma B E, Boppart S A, Golubovic B, Swanson E A, Fujimoto J G. Rapid acquisition of in vivo biological images using optical coherence tomography. Opt. Lett. 21:1408-1410, 1996.

22. Chen Z, Milner T E, Srinivas S, Wang X. Noninvasive imaging of in vivo blood flow velocity using optical Doppler tomography. Opt. Lett. 22:1119-1121, 1997.

23. Yazdanfar S, Kulkarni M D, Izatt J A. High resolution imaging of in vivo cardiac dynamics using color Doppler optical coherence tomography. Opt. Express. 1:424-431, 1997.

24. de Boer J F, Milner T E, van Germert M J C, Nelson S J. Two-dimensional birefringence imaging in biological tissue by polarization sensitive optical coherence tomography. Opt. Lett. 22:934-936, 1997.

25. Tearney G J, Boppart S A, Bouma B E, Brezinski M E, Weissman N J, Southern J F, Fujimoto J G. Scanning single-mode fiber optic catheter-endoscope for optical coherence tomography. Opt. Lett. 21:1-3, 1996.

26. Boppart S A, Bouma B E, Pitris C, Tearney G J, Fujimoto J G. Forward-imaging instruments for optical coherence tomography. Opt. Lett. 22:1618-1620, 1997.

27. Tearney G J, Brezinski M E, Bouma B E, Boppart S A, Pitris C, Southern J F, Fujimoto J G. In vivo endoscopic optical biopsy with optical coherence tomography. Science 276:2037-2039, 1997.

28. Bouma B E, Tearney G J, Compton CC, Nishioka N S. High-resolution imaging of the human esophagus and stomach in vivo using optical coherence tomography. Gastrointest. Endosc. 51:467-474, 2000.

29. Sivak M V Jr, Kobayashi K, Izatt J A, Rollins A M, Ung-Runyawee R, Chak A, Wong R C, Isenberg G A, Willis J. High-resolution endoscopic imaging of the gastrointestinal tract using optical coherence tomography. Gastrointest. Endosc. 51:474-479, 2000.

30. Li X, Boppart S A, Van Dam J, Mashimo H, Mutinga M, Drexler W, Klein M, Pitris C, Krinsky M L, Brezinski M E, Fujimoto J G. Optical coherence tomography: advanced technology for the endoscopic imaging of Barrett's esophagus. Endoscopy 32:921-930, 2000.

31. Boppart S A, Brezinski M E, Bouma B E, Tearney G J, Fujimoto J G. Investigation of developing embryonic morphology using optical coherence tomography. Dev. Biol. 177:54-63, 1996.

32. Boppart S A, Brezinski M E, Tearney G J, Bouma B E, Fujimoto J G. Imaging developing neural morphology using optical coherence tomography. J. Neurosci. Meth. 2112:65-72, 1996.

33. Boppart S A, Tearney G J, Bouma B E, Southern J F, Brezinski M E, Fujimoto J G. Noninvasive assessment of the developing *Xenopus* cardiovascular system using optical coherence tomography. Proc. Natl. Acad. Sci. USA 94:4256-4261, 1997.

34. Boppart S A, Bouma B E, Pitris C, Southern J F, Brezinski M E, Fujimoto J G. In vivo cellular optical coherence tomography imaging. Nature Med. 4:861-864, 1998.

35. Pitris C, Goodman A K, Boppart S A, Libus J J, Fujimoto J G, Brezinski M E. High resolution imaging of gynecological neoplasms using optical coherence tomography. Obstet. Gynecol. 93:135-139, 1999.

36. Pitris C, Jesser C, Boppart S A, Stamper D, Brezinski M E, Fujimoto J G. Feasibility of optical coherence tomography for high resolution imaging of human gastrointestinal tract malignancies. J. Gastroenterol. 35:87-92, 1999.

37. Boppart S A. *Surgical Diagnostics, Guidance, and Intervention using Optical Coherence Tomography*. Ph.D. Thesis. Harvard-MIT Division of Health Sciences and Technology, Department of Electrical Engineering and Computer Science, Massachusetts Institute of Technology, Cambridge, Mass., 1998.

The invention claimed is:

1. A method of examining a sample, comprising:
   exposing a non-linear reference medium to a first set of electromagnetic radiation generated in an interferometric system to form a second set of electromagnetic radiation scattered from the non-linear reference medium;
   exposing a sample to a third set of electromagnetic radiation to form a fourth set of electromagnetic radiation scattered from the sample; and interfering the second set of electromagnetic radiation and the fourth set of electromagnetic radiation; and
   detecting fourth photos in the fourth set of electromagnetic radiation;
   wherein the detecting comprises interfering;
   wherein the fourth photons are anti-Stokes photons or Stokes photons;
   wherein the first set and the third set of electromagnetic radiation are generated from a source;

at least a portion of the second set of electromagnetic radiation is of a frequency different from that of the first set of electromagnetic radiation; and at least a portion of the fourth set of electromagnetic radiation is of a frequency different from that of the third set of electromagnetic radiation.

2. The method of claim 1, wherein the fourth photons are anti-Stokes photons.

3. The method of claim 1, wherein the fourth photons are Stokes photons.

4. A method of forming an image of a sample, comprising:
exposing a non-linear reference medium to a first set of electromagnetic radiation generated in an interferometric system to form a second set of electromagnetic radiation scattered from the non-linear reference medium;
exposing a sample to a third set of electromagnetic radiation to form a fourth set of electromagnetic radiation scattered from the sample;
forming a digital data set corresponding to the sample; and
converting the data set into an image;
wherein the forming of the data set comprises interfering the second set of electromagnetic radiation and the fourth set of electromagnetic radiation;
the first set and the third set of electromagnetic radiation are generated from a source;
at least a portion of the second set of electromagnetic radiation is of a frequency different from that of the first set of electromagnetic radiation; and
at least a portion of the fourth set of electromagnetic radiation is of a frequency different from that of the third set of electromagnetic radiation.

5. The method of claim 4, wherein the fourth photons are anti-Stokes photons.

6. The method of claim 1, wherein the electromagnetic radiation is in the frequency range of infra-red to ultraviolet light.

7. The method of claim 4, wherein the electromagnetic radiation is in the frequency range of infra-red to ultraviolet light.

8. The method of claim 1, wherein the examining of the sample is by optical coherence tomography.

9. The method of claim 4, wherein the forming of the data set is by optical coherence tomography.

10. The method of claim 1, wherein the sample is selected from the group consisting of a tissue sample, a single cell, and a patient.

11. The method of claim 4, wherein the sample is selected from the group consisting of a tissue sample, a single cell, and a patient.

12. The method of claim 10, wherein the sample is a human patient.

13. The method of claim 11, wherein the sample is a human patient.

14. In a method of forming an image using an optical coherence tomography, apparatus, the method including exposing a sample or patient to electromagnetic radiation, collecting scattered electromagnetic radiation, and forming an image from the collected electromagnetic radiation including interfering the collected electromagnetic radiation with reference electromagnetic radiation, the improvement comprising the reference electromagnetic radiation being scattered from a non-linear reference sample, and the wavelength of the collected electromagnetic radiation being different from that of the electromagnetic radiation that the sample or patient is exposed to.

15. In an optical coherence tomography device, including an electromagnetic radiation source for generating reference electromagnetic radiation and sample electromagnetic radiation, an optical delay line, a scanner, and a electromagnetic radiation detector, the improvement comprising a reference holder and optics adapted for exposing the reference electromagnetic radiation to a non-linear reference medium before interfering the reference electromagnetic radiation with the sample electromagnetic radiation.

16. A device for examining a sample, comprising:
an oscillator,
a reference generator, including non-linear reference medium, a optically coupled to the oscillator,
a sample illuminator, optically coupled to the oscillator,
an interferometric demodulator, optically coupled to the reference generator and the sample illuminator,
a recorder, coupled to the demodulator, and
a frequency-selecting element that ensures that the light that illuminates the sample is excluded from the modulator.

17. The device of claim 16, wherein the oscillator comprises a laser.

18. The device of claim 17, wherein the oscillator further comprises a pulse shaper or a chirper.

19. The device of claim 16, further comprising a scanner for scanning a sample, coupled to the sample illuminator.

20. A method of examining a sample, comprising:
exposing sample to a first set of electromagnetic radiation generated in an interferometric system to form a second set of electromagnetic radiation non-linearly scattered from the sample; and
interfering the second set of electromagnetic radiation with a third set of electromagnetic radiation;
wherein the third set of electromagnetic radiation is coherent with the first set of electromagnetic radiation;
at least a first portion of the second set of electromagnetic radiation is of a frequency different from that of the first set of electromagnetic radiation; and
at least a portion of the third set of electromagnetic radiation is of the same frequency as the first portion of the second set of electromagnetic radiation.

21. The method of claim 20, further comprising detecting second photons in the second set of electromagnetic radiation; wherein the detecting comprises the interfering.

22. The method of claim 21, wherein the second photons are anti-Stokes photons.

23. A method of forming an image of a sample, comprising:
exposing a sample to a first set of electromagnetic radiation generated in an interferometric system to form a second set of electromagnetic radiation non-linearly scattered from the sample;
forming a digital data set corresponding to the sample; and
converting the data set into an image;
wherein the forming of the image comprises interfering the second set of electromagnetic radiation and a third set of electromagnetic radiation;
wherein the third set of electromagnetic radiation is phase-coherent with the first set of electromagnetic radiation;
at least a first portion of the second set of electromagnetic radiation is of a frequency different from that of the first set of electromagnetic radiation; and
at least a portion of the third set of electromagnetic radiation is of the same frequency as the first portion of the second set of electromagnetic radiation.

24. The method of claim 23, further comprising detecting second photons in the second set of electromagnetic radiation; wherein the detecting comprises the interfering, and the forming of the image comprises the detecting.

25. The method of claim 23, wherein the second photons are anti-Stokes photons.

26. The method of claim 23, wherein the second photons are Stokes photons.

27. The method of claim 20, wherein the electromagnetic radiation is in the frequency range of infra-red to ultraviolet light.

28. The method of claim 23, wherein the electromagnetic radiation is in the frequency range of infra-red to ultraviolet light.

29. The method of claim 20, wherein the examining of the sample is by optical coherence tomography.

30. The method of claim 23, wherein the forming of the image is by optical coherence tomography.

31. The method of claim 20, wherein the sample is selected from the group consisting of a tissue sample, a single cell, and a patient.

32. The method of claim 23, wherein the sample is selected from the group consisting of a tissue sample, a single cell, and a patient.

33. The method of claim 31, wherein the sample is a human patient.

34. The method of claim 32, wherein the sample is a human patient.

35. A method of examining a sample, comprising:
exposing a non-linear reference medium to a first set of electromagnetic radiation generated in an interferometric system to form a second set of electromagnetic radiation inelastically scattered from the non-linear reference;
exposing a sample to a third set of electromagnetic radiation to form a fourth set of electromagnetic radiation scattered from the sample; and
interfering the second set of electromagnetic radiation and the fourth set of electromagnetic radiation;
wherein the first set and the third set of electromagnetic radiation are generated from a source;
at least a portion of the second set of electromagnetic radiation is of a frequency different from that of the first set of electromagnetic radiation; and
at least a portion of the fourth set of electromagnetic radiation is of a frequency different from that of the third set of electromagnetic radiation.

* * * * *

UNITED STATES PATENT AND TRADEMARK OFFICE
CERTIFICATE OF CORRECTION

PATENT NO. : 7,623,908 B2
APPLICATION NO. : 10/717437
DATED : November 24, 2009
INVENTOR(S) : Stephen A. Boppart et al.

It is certified that error appears in the above-identified patent and that said Letters Patent is hereby corrected as shown below:

In Col. 26, line 10
replace "including non-linear"
with "including a non-linear".

In Col. 26, line 11
replace "a optically coupled"
with "optically coupled".

In Col. 26, line 26
replace "exposing sample"
with "exposing the sample".

Signed and Sealed this

Twelfth Day of January, 2010

David J. Kappos
*Director of the United States Patent and Trademark Office*

UNITED STATES PATENT AND TRADEMARK OFFICE
CERTIFICATE OF CORRECTION

PATENT NO. : 7,623,908 B2  Page 1 of 1
APPLICATION NO. : 10/717437
DATED : November 24, 2009
INVENTOR(S) : Boppart et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1580 days.

Signed and Sealed this

Twenty-sixth Day of October, 2010

David J. Kappos
*Director of the United States Patent and Trademark Office*